(12) United States Patent
Flavell et al.

(10) Patent No.: US 9,095,126 B2
(45) Date of Patent: Aug. 4, 2015

(54) TARGETING TGF-β AS A THERAPY FOR ALZHEIMER'S DISEASE

(75) Inventors: Richard A. Flavell, Guilford, CT (US); Terrence C. Town, Bel-Air, CA (US)

(73) Assignee: Yale University, New Haven, CT (US)

( * ) Notice: Subject to any disclaimer, the term of this patent is extended or adjusted under 35 U.S.C. 154(b) by 243 days.

(21) Appl. No.: 12/994,412

(22) PCT Filed: May 26, 2009

(86) PCT No.: PCT/US2009/045156
§ 371 (c)(1),
(2), (4) Date: Feb. 22, 2011

(87) PCT Pub. No.: WO2009/146301
PCT Pub. Date: Dec. 3, 2009

(65) Prior Publication Data
US 2011/0136892 A1    Jun. 9, 2011

Related U.S. Application Data

(60) Provisional application No. 61/128,970, filed on May 27, 2008, provisional application No. 61/057,042, filed on May 29, 2008.

(51) Int. Cl.
| | |
|---|---|
| *A01K 67/027* | (2006.01) |
| *A61K 38/18* | (2006.01) |
| *C07K 14/47* | (2006.01) |
| *C07K 14/71* | (2006.01) |
| *C12N 15/85* | (2006.01) |

(52) U.S. Cl.
CPC ......... *A01K 67/0275* (2013.01); *A61K 38/1841* (2013.01); *C07K 14/4711* (2013.01); *C07K 14/71* (2013.01); *C12N 15/8509* (2013.01); *A01K 2217/052* (2013.01); *A01K 2217/056* (2013.01); *A01K 2217/15* (2013.01); *A01K 2217/206* (2013.01); *A01K 2227/105* (2013.01); *A01K 2267/0312* (2013.01); *A61K 2300/00* (2013.01); *C12N 2830/008* (2013.01)

(58) Field of Classification Search
CPC ............... A61K 39/39533; C07K 14/4711; C07K 14/71
See application file for complete search history.

(56) References Cited

U.S. PATENT DOCUMENTS

| | | | |
|---|---|---|---|
| 2005/0261299 A1* | 11/2005 | Kim et al. ...................... | 514/249 |
| 2006/0229233 A1 | 10/2006 | Frenkel et al. | |
| 2007/0142408 A1 | 6/2007 | Scarborough et al. | |
| 2008/0031911 A1 | 2/2008 | He et al. | |

FOREIGN PATENT DOCUMENTS

| | | |
|---|---|---|
| WO | WO02/40468 | 5/2002 |
| WO | WO2005/074981 | 8/2005 |

OTHER PUBLICATIONS

Sigma 2014 "SB-505124 hydrochloride hydrate" product description. Downloaded from www.sigmaaldrich.com on Apr. 25, 2014.*
Wyss-Coray 2006 "TGF-β pathway as a potential target in neurodegeneration and Alzheimer's" Curr Alz Research 3:191-195.*
Ajami et al., "Local self-renewal can sustain CNS microglia maintenance and function throughout adult life." 2007, Nat. Neurosci 10:1538-1543.
Akiyama, et al. "Inflammation and Alzheimer's disease." 2000, Neurobiol Aging. 21(3):383-421.
Bacskai et al., "Imaging of amyloid-beta deposits in brains of living mice permits direct observation of clearance of plaques with immunotherapy." 2001 Nat. Med. 7(3): 369-72.
Bard et al., "Peripherally administered antibodies against amyloid-peptide enter the central nervous system and reduce pathology in a mouse model of Alzheimer disease" 2000 Nat. Med. 6: 916-19.
Brionne et al.,"Loss of TGF-beta 1 leads to increased neuronal cell death and microgliosis in mouse brain." 2003, Neuron. 40(6):1133-45.
Callahan et al., "Augmented senile plaque load in aged female beta-amyloid precursor protein-transgenic mice." 2001, Am J Pathol. 158(3):1173-7.
Demattos et al., "Brain to plasma amyloid-beta efflux: a measure of brain amyloid burden in a mouse model of Alzheimer's disease." 2002, Science 295:2264-2267.
El Khoury et al., "Ccr2 deficiency impairs microglial accumulation and accelerates progression of Alzheimer-like disease." 2007, Nat. Med 13:432-438.
Ellis et al., "Cerebral amyloid angiopathy in the brains of patients with Alzheimer's disease: the CERAD experience, Part XV." 1996, Neurology. 46(6):1592-6.
Hardy and Allsop "Amyloid deposition as the central event in the aetiology of Alzheimer's disease." 1991 Trends Pharmacol. Sci. 12:383-388.
Holcomb et al., "Accelerated Alzheimer-type phenotype in transgenic mice carrying both mutant amyloid precursor protein and presenilin 1 transgenes." 1998 Nat. Med. 4: 97-100.
Holcomb et al., "Behavioral Changes in Transgenic Mice Expressing Both Amyloid Precursor Protein and Presenilin-1 Mutations: Lack of Association with Amyloid Deposits" 1999 Behav. Genet. 29: 177-185.
Hsiao, et al. "Correlative memory deficits, Abeta elevation, and amyloid plaques in transgenic mice." 1996, Science 274(5284):99-102.

(Continued)

*Primary Examiner* — Gregory S Emch
*Assistant Examiner* — Adam M Weidner
(74) *Attorney, Agent, or Firm* — Riverside Law LLP

(57) ABSTRACT

Described herein are compositions and methods for enhancing peripheral macrophage Aβ phagocytosis activity. The methods include inhibiting the TGF-β signaling pathway and activating the BMP signaling pathway in peripheral macrophages to promote central nervous system infiltration and enhance macrophage Aβ phagocytosis activity. Inhibition of TGF-β signaling and activation of BMP signaling in peripheral macrophages represents an advantageous anti-amyloid therapeutic approach for Alzheimer's disease.

3 Claims, 31 Drawing Sheets

(56) References Cited

OTHER PUBLICATIONS

Irizarry et al., APPSw transgenic mice develop age-related A beta deposits and neuropil abnormalities, but no neuronal loss in CA1. 1997, J Neuropathol Exp Neurol. 56(9):965-73.
Jankowsky et al., "Co-expression of multiple transgenes in mouse CNS: a comparison of strategies." 2001, Biomol. Eng 17:157-165.
Janus et al, "A beta peptide immunization reduces behavioural impairment and plaques in a model of Alzheimer's disease." 2000 Nature 408: 979-82.
Juedes, A.E. & Ruddle, "Resident and Infiltrating Central Nervous System APCs Regulate the Emergence and Resolution of Experimental Autoimmune Encephalomyelitis" 2001 J. Immunol. 166: 5168-5175.
King et al., "Progressive and gender-dependent cognitive impairment in the APPsw transgenic mouse model for Alzheimer's disease" 1999, Behav Brain Res. 103(2)145-62.
Laouar et al., "Transforming growth factor-beta controls T helper type 1 cell development through regulation of natural killer cell interferon-gamma." 2005, Nat Immunol. 6(6):600-7.
Lemere et al., "Nasal A beta treatment induces anti-A beta antibody production and decreases cerebral amyloid burden in PD-APP mice." 2000, Ann. NY Acad. Sci 920:328-331.
Li et al.,"Transforming growth factor-beta regulation of immune responses." 2006, Annu Rev Immunol. 24:99-146.
Mildner et al., "Microglia in the adult brain arise from Ly-6ChiCCR2+ monocytes only under defined host conditions." 2007, Nat. Neurosci 10:1544-1653.
Morgan et al. "A beta peptide vaccination prevents memory loss in an animal model of Alzheimer's disease.", 2000 Nature 408: 982-5.
Moustakas, et al., "Non-Smad TGF-β signals" 2005, J Cell Sci 118:3573-3585.
Nicoll et al., "Neuropathology of human Alzheimer disease after immunization with amyloid-beta peptide: a case report." 2003, Nat. Med 9:448-452.
Pittenger et al., "Reversible inhibition of CREB/ATF transcription factors in region CA1 of the dorsal hippocampus disrupts hippocampus-dependent spatial memory." 2002 Neuron 34: 447-462.
Robbins et al., "Kinetics of cerebral amyloid angiopathy progression in a transgenic mouse model of Alzheimer disease." 2006, J. Neurosci 26:365-371.
Schenk et al., "Immunization with amyloid-attenuates Alzheimer-disease-like pathology in the PDAPP mouse" 1999 Nature 400: 173-177.
Selkoe, "Alzheimer's disease: genes, proteins, and therapy." 2001, Physiol Rev. 81(2):741-66.
Simard et al., "Bone marrow-derived microglia play a critical role in restricting senile plaque formation in Alzheimer's disease." 2006, Neuron 49:489-502.
Stalder et al., "Invasion of hematopoietic cells into the brain of amyloid precursor protein transgenic mice," 2005, J. Neurosci 25:11125-11132.
Tan et al., "Microglial Activation Resulting from CD40-CD40L Interaction After β-Amyloid Stimulation" 1999 Science 286: 2352-2355.
Tan et al., "Role of CD40 ligand in amyloidosis in transgenic Alzheimer's mice." 2002, Nat. Neurosci 5:1288-1293.
Tesseur et al., "Deficiency in neuronal TGF-beta signaling promotes neurodegeneration and Alzheimer's pathology." 2006, J Clin Invest. 116(11):3060-9.
Town et al., "The microglial "activation" continuum: from innate to adaptive responses." 2005, J. Neuroinflammation 2:24.
Town et al., "Microglia recognize double-stranded RNA via TLR3." 2006 J. Immunol. 176: 3804-3812.
Town et al., "Blocking TGF-beta-Smad2/3 innate immune signaling mitigates Alzheimer-like pathology." 2008, Nat Med 14(6):681-7.
Westerman et al., "The relationship between Abeta and memory in the Tg2576 mouse model of Alzheimer's disease." 2002, J. Neurosci 22:1858-1867.
Wisniewski et al., "Ultrastructural studies of the cells forming amyloid fibers in classical plaques." 1989, Can J Neurol Sci. 16(4 Suppl):535-42.
Wyss-Coray et al., "Amyloidogenic role of cytokine TGF-beta1 in transgenic mice and in Alzheimer's disease." 1997 Nature 389: 603-606.
Wyss-Coray et al., "Chronic overproduction of transforming growth factor-beta1 by astrocytes promotes Alzheimer's disease-like microvascular degeneration in transgenic mice." 2000 Am. J. Pathol. 156: 139-150.
Wyss-Coray et al., "TGF-beta1 promotes microglial amyloid-beta clearance and reduces plaque burden in transgenic mice." 2001 Nat. Med. 7(5): 612-618.
Tesseur et al., "Deficiency in neuronal TGF-beta signaling promotes neurodegeneration and Alzheimer's pathology." 2006 J Clin Invest 116(11):3060-3069.
Salins et al., "TGF-beta1 is increased in a transgenic mouse model of familial Alzheimer's disease and causes neuronal apoptosis." 2007, Neuroscience Letters 430(2004):81-86.

* cited by examiner

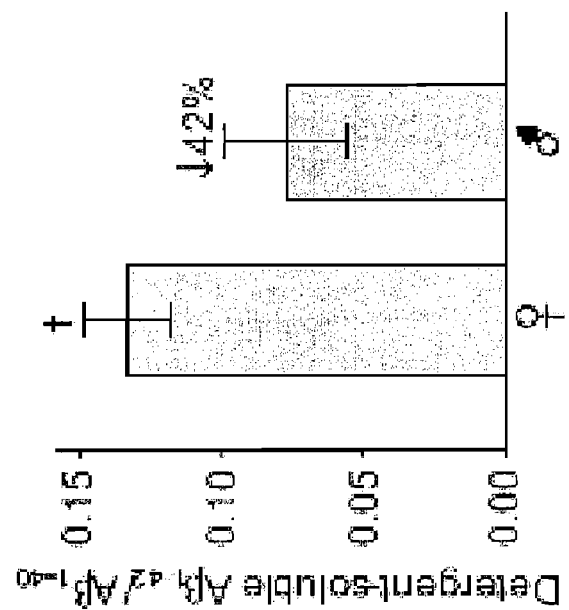
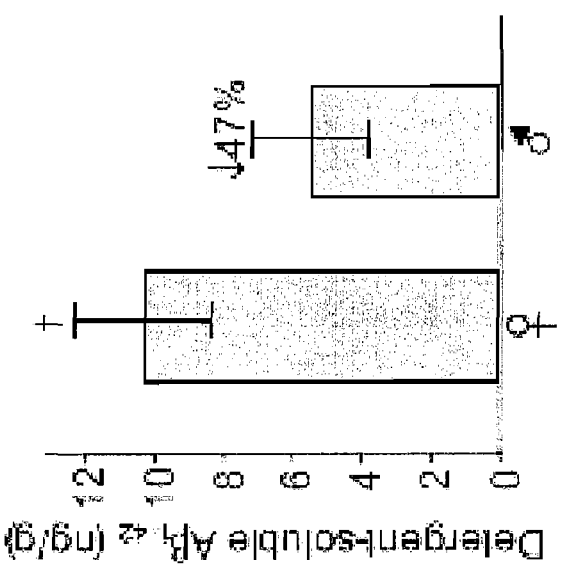
Figure 9

| Test | Activity | Y-maze | | | Behavioral Assay | | | | | | |
|---|---|---|---|---|---|---|---|---|---|---|---|
| | | | | | | Morris water maze | | | | | |
| | | | | | | Probe trial day 5 | | | Probe trial day 10 | | |
| Measure | Distance traveled | Arm entries | % alternation | Latency | goal quadrant occupancy | goal platform crossings | % goal platform crossings | goal quadrant occupancy | goal platform crossings | % goal platform crossings |
| Genotype groups | 3 | 3 | 3 | 2 | 2 | 2 | 2 | 2 | 2 | 2 |
| Variables | | | | | | | | | | |
| gender | $F_{(1,34)}=0.01$ $p=0.93$ | $F_{(1,33)}=2.43$ $p=0.13$ | $F_{(1,33)}=1.09$ $p=0.31$ | $F_{(1,35)}=3.88$ $p=0.06$ | $F_{(1,35)}=0.10$ $p=0.76$ | $F_{(1,35)}=1.89$ $p=0.18$ | $F_{(1,35)}=0.19$ $p=0.67$ | $F_{(1,35)}=0.34$ $p=0.57$ | $F_{(1,35)}=0.53$ $p=0.47$ | $F_{(1,35)}=0.44$ $p=0.51$ |
| time | $F_{(3.8,129.8)}=7.96$ $p<0.001$ | - | - | $F_{(9,315)}=8.69$ $p<0.001$ | - | - | - | - | - | - |
| genotype | $F_{(2,34)}=4.61$ $p<0.05$ | $F_{(2,33)}=7.61$ $p<0.01$ | $F_{(2,33)}=4.05$ $p<0.05$ | $F_{(1,35)}=10.81$ $p<0.01$ | $F_{(1,35)}=1.46$ $p=0.24$ | $F_{(1,35)}=1.83$ $p=0.19$ | $F_{(1,35)}=0.51$ $p=0.48$ | $F_{(1,35)}=1.65$ $p=0.21$ | $F_{(1,35)}=0.09$ $p=0.77$ | $F_{(1,35)}=0.0001$ $p=0.99$ |
| gender X genotype | $F_{(2,34)}=0.27$ $p=0.77$ | $F_{(2,33)}=0.22$ $p=0.81$ | $F_{(2,33)}=0.31$ $p=0.74$ | $F_{(1,35)}=1.49$ $p=0.23$ | $F_{(1,35)}=2.81$ $p=0.10$ | $F_{(1,35)}=2.13$ $p=0.15$ | $F_{(1,35)}=0.90$ $p=0.35$ | $F_{(1,35)}=5.24$ $p=0.03$ | $F_{(1,35)}=2.09$ $p=0.16$ | $F_{(1,35)}=2.34$ $p=0.14$ |
| genotype X time | $F_{(7.6,129.8)}=1.22$ $p=0.30$ | - | - | $F_{(9,315)}=1.22$ $p=0.28$ | - | - | - | - | - | - |
| gender X time | $F_{(3.8,129.8)}=1.37$ $p=0.25$ | - | - | $F_{(9,315)}=1.33$ $p=0.22$ | - | - | - | - | - | - |
| gender X genotype X time | $F_{(7.6,129.8)}=0.89$ $p=0.53$ | - | - | $F_{(9,315)}=0.62$ $p=0.78$ | - | - | - | - | - | - |

Figure 10

| Mouse ID | Genotype | Score |
|---|---|---|
| 02 | +/+ | ++ |
| 03 | +/+ | ++ |
| 05 | +/− | − |
| 09 | +/− | +/− |
| 10 | +/− | +/− |
| 13 | +/+ | ++ |
| 28 | +/− | − |
| 41 | +/+ | +++ |
| 49 | +/+ | +++ |
| 50 | +/− | − |

Figure 11

TARGETING TGF-β AS A THERAPY FOR ALZHEIMER'S DISEASE

CROSS-REFERENCE TO RELATED APPLICATIONS

The present application is a 35 U.S.C. §371 national phase application from, and claiming priority to, International Application PCT/US2009/045156, filed May 26, 2009, which claims priority under 35 U.S.C. §119(e) to U.S. Patent Application Nos. 61/128,970, filed May 27, 2008, and 61/057,042, filed May 29, 2008, the disclosures of which are incorporated by reference herein as if each is being set forth herein in its entirety.

STATEMENT REGARDING FEDERALLY SUPPORTED RESEARCH OR DEVELOPMENT

This invention was made with government support under AG029726 awarded by National Institutes of Health. The government has certain rights in the invention.

BACKGROUND OF THE INVENTION

Alzheimer's disease is characterized by senile (neuritic) plaques, neurofibrillary tangles, and loss of neural cells in the brain. In particular, β-amyloid deposited in senile plaques is considered to play a central role in the pathoetiology of Alzheimer's disease. β-Amyloid peptide (Aβ), the major component of β-amyloid deposits, is produced by metabolism of β-amyloid precursor protein (βAPP) by β- and γ-secretases in neural cells.

Alzheimer's disease is characterized by deposition in the brain of the 40-42-amino-acid Aβ peptide, which is proteolytically derived from amyloid precursor protein (APP), resulting in cerebral β-amyloid plaques (Selkoe, 2001, Physiol Rev. 81 (2):741-66). Despite low-level, chronic activation of innate immunity in Alzheimer's disease (Akiyama, et al. 2000, Neurobiol Aging. 21 (3):383-421), microglia, the brain's chief resident immune cells, ultimately do not clear β-amyloid deposits (Wisniewski et al., 1989, Can J Neurol Sci. 16 (4 Suppl):535-42).

It has been disclosed that the formation of senile plaques was suppressed and the number of existing senile plaques was reduced by administering Aβ peptide along with an adjuvant for immunization to transgenic mice which have pathological features of Alzheimer's disease and overexpress a human amyloid APP transgene (Schenk et al., 1999 Nature 400: 173-177).

Furthermore, it is known that the cytokine TGF-β1 (transforming growth factor β1) is overexpressed in brains of patients with Alzheimer's disease compared with healthy elderly and TGF-β1 promotes the production of inflammatory cytokines (IL-1β (interleukin-1β), TNF-α (tumor necrosis factor-α and the like) in vascular endothelial cells. Further, it has been reported that TGF-β1 promoted Alzheimer's disease-related pathological changes such as cerebrovascular amyloid deposition and microvascular degeneration (Wyss-Coray et al., 1997 Nature 389: 603-606; Wyss-Coray et al., 2000 Am. J. Pathol. 156: 139-150; Wyss-Coray et al., 2001 Nat. Med. 7: 612-618).

TGF-βs are pleiotropic cytokines with central roles in immune suppression, immune homeostasis and repair after injury (Li et al., 2006, Annu Rev Immunol. 24:99-146). TGF-β1 in brain dampens microglial activation (Brionne et al., 2003, Neuron. 40 (6):1133-45). However, TGF-β1 overexpression promotes brain inflammation (Wyss-Coray et al., 2000 Am J Pathol. 156 (1):139-50), simultaneously accelerates brain vascular β-amyloid deposits and reduces parenchymal β-amyloid deposits (Wyss-Coray et al., 1997, Nature 389: 603-6; Wyss-Coray, et al., 2001, Nat Med. 7 (5):612-8), and elicits neuronal Aβ secretion (Tesseur et al., 2006, J Clin Invest. 116 (10:3060-9).

Recent studies indicate that the relationship between microglial activation and promotion of AD-like pathology is not straightforward, as some forms of microglial activation appear to mitigate this pathology. It has been shown that immunization of the PDAPP mouse model of AD with Aβ$_{1-42}$ results in marked reduction of Aβ deposits, and atypical punctate structures containing Aβ that resembled activated microglia were found in brains of these mice, suggesting that immunization activates microglia to phagocytose Aβ (Schenk et al., 1999 Nature 400: 173-7). This hypothesis was further supported ex vivo, where microglia were shown to clear deposited Aβ that was opsonized by anti-Aβ antibodies (Bard et al., 2000 Nat. Med. 6: 916-19). Similar prophylactic effects of Aβ$_{1-42}$ immunization have now been independently observed in other transgenic mouse models of AD (Morgan et al., 2000 Nature 408: 982-5; Janus et al, 2000 Nature 408: 979-82), and in vivo visualization has shown that application of anti-Aβ antibody to PDAPP mouse brain results in rapid Aβ plaque clearance associated with marked local microglial activation (as measured by lectin immunoreactivity) (Bacskai et al., 2001 Nat. Med. 7: 369-72). In addition, bigenic mice that overexpress human APP and TGF-β1 also demonstrate reduced parenchymal Aβ deposition associated with an increase in microglia positive for the F4/80 antigen (Wyss-Coray et al., 2001 Nat. Med. 7: 612-18).

Therapeutic agents for Alzheimer's disease should be able to suppress senile plaque formation and amyloid deposition in the central nervous system and at the same time should not cause side effects such as encephalitis. Remediation of cerebral amyloidosis, including soluble and deposited forms of Aβ peptides, should prevent downstream pathological events as predicted by the "amyloid cascade hypothesis" of Alzheimer's disease (Hardy and Allsop, 1991 Trends Pharmacol. Sci. 12:383-388). There exists a need in the art to develop new medications for Alzheimer's disease.

SUMMARY OF THE INVENTION

The present invention provides a method of enhancing macrophage Aβ phagocytosis activity. The method comprises inhibiting a component of transforming growth factor-β (TGF-β) signaling pathway in a macrophage comprising contacting a macrophage with an inhibitor of a component of the TGF-β signaling pathway. Preferably, the TGF-β signaling pathway is TGF-β-Smad2/3 signaling pathway.

In one embodiment, the inhibitor of a component of TGF-β signaling pathway is selected from the group consisting of a small interfering RNA (siRNA), a microRNA, an antisense nucleic acid, a ribozyme, an expression vector encoding a transdominant negative mutant, an antibody, a peptide, and a small molecule.

In one embodiment, the inhibitor of a component of TGF-β signaling pathway inhibits activin-like kinase 5 (ALK5).

In yet another embodiment, the method of enhancing macrophage Aβ phagocytosis activity further comprises contacting the macrophage with an activator of a component of bone morphogenic protein-Smad1/5/8-PAK2 signaling pathway.

The invention also provides a method of enhancing macrophage Aβ phagocytosis activity comprising activating a component of bone morphogenie protein-Smad1/5/8-PAK2 signaling pathway in a macrophage comprising contacting the macrophage with an activator of a component of bone morphogenic protein-Smad1/5/8-PAK2 signaling pathway.

In one embodiment, the method further comprises contacting the macrophage with an inhibitor of a component of TGF-β signaling pathway. Preferably, the TGF-β signaling pathway is TGF-β-Smad2/3 signaling pathway.

In one embodiment, the inhibitor of a component of TGF-β signaling pathway is selected from the group consisting of a small interfering RNA (siRNA), a microRNA, an antisense nucleic acid, a ribozyme, an expression vector encoding a transdominant negative mutant, an antibody, a peptide, and a small molecule.

In yet another embodiment, the inhibitor of a component of TGF-β signaling pathway inhibits activin-like kinase 5 (ALK5).

The invention also provides a method of increasing Aβ clearance from a CNS tissue. The method comprises inducing peripheral macrophages to infiltrate into the brain, wherein the macrophages exhibit enhanced Aβ phagocytosis activity.

In one embodiment, the peripheral macrophages have been modified to have a component of transforming growth factor-β (TGF-β) signaling pathway inhibited with an inhibitor of a component of TGF-β signaling pathway. Preferably, the TGF-β signaling pathway is TGF-β-Smad2/3 signaling pathway.

In another embodiment, the inhibitor of a component of TGF-β signaling pathway is selected from the group consisting of a small interfering RNA (siRNA), a microRNA, an antisense nucleic acid, a ribozyme, an expression vector encoding a transdominant negative mutant, an antibody, a peptide, and a small molecule.

In yet another embodiment, the inhibitor of a component of TGP-β signaling pathway inhibits activin-like kinase 5 (ALK5).

In one embodiment, the peripheral macrophages have been modified to have a component of bone morphogenie protein-Smad1/5/8-PAK2 signaling pathway activated.

In another embodiment, the peripheral macrophages have been modified to have a component of transforming growth factor-β (TGF-β) signaling pathway inhibited and a component of bone morphogenic protein-Smad1/5/8-PAK2 signaling pathway activated.

In one embodiment, the infiltrating macrophages are shifted to an anti-inflammatory phenotype endorsing Aβ phagocytosis.

The invention also provides a method of treating or preventing Alzheimer's disease in a mammal. The method comprises inducing peripheral macrophages to infiltrate into the CNS of a mammal, wherein the macrophages exhibit enhance Aβ phagocytosis activity.

In one embodiment, the peripheral macrophages have been modified to have a component of transforming growth factor-β (TGF-β) signaling pathway inhibited with an inhibitor of a component of TGF-β signaling pathway. Preferably, the TGF-β signaling pathway is TGF-β-Smad2/3 signaling pathway.

In one embodiment, the inhibitor of a component of TGF-β signaling pathway is selected from the group consisting of a small interfering RNA (siRNA), a microRNA, an antisense nucleic acid, a ribozyme, an expression vector encoding a transdominant negative mutant, an antibody, a peptide, and a small molecule.

In another embodiment, the inhibitor of a component of TGF-β signaling pathway inhibits activin-like kinase 5 (ALK5).

In yet another embodiment, the peripheral macrophages have been modified to have a component of bone morphogenic protein-Smad1/5/8-PAK2 signaling pathway activated.

In another embodiment, the peripheral macrophages have been modified to have a component of transforming growth factor-β (TGF-β) signaling pathway inhibited and a component of bone morphogenic protein-Smad1/5/8-PAK2 signaling pathway activated.

In one embodiment, the infiltrating macrophages are shifted to an anti-inflammatory phenotype endorsing Aβ phagocytosis.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1D, is a series of images demonstrating reduced behavioral impairment in Tg2576-CD11c-DNR mice at 16-17 months of age. Four groups of littermate mice, including wild-type (WT, n=13), CD11c-DNR (n=6), Tg2576 (n=11) and Tg2576-CD11c-DNR (n=9) mice, were subjected to behavioral testing. Mice were individually placed into a novel environment, and the distance traveled in cm (y axis) is represented over a 20-min time course in bins of 2.5 min each (x axis) (FIG. 1A). Mice were individually placed into a radially symmetric Y-maze and total number of arm entries (y axis) is shown for each genotype (x axis) (FIG. 1B). Number of mice (y axis) are shown grouped by bins of arm entries (10 entries per bin, x axis; Gaussian curves are shown for each mouse group) in the Y-maze (FIG. 1C). Percentage alternation between Y-maze arms (y axis; chance level is shown with the dotted line) is represented for each genotype (x axis) (FIG. 1D). Data are represented as group means±s.e.m. For FIG. 1C, there is a rightward shift of the Tg2576 mouse group relative to WT and CD11c-DNR littermate controls (combined as they did not significantly differ) and to the Tg2576-CD11c-DNR mouse group. All post hoc statistical comparisons are versus Tg2576 mice, *P<0.001, P<0.01, *P<0.05, †P<0.10. No significant difference was found between WT and CD11c-DNR mouse groups (P>0.05).

FIGS. 2A-2E, is a series of images depicting Gender- and Tg2576 transgene-dependent Morris water maze impairment and β-amyloid plaque reduction in Tg2576/CD11c-DNR vs. Tg2576 mice. FIGS. 2A-2C depicts escape latency (measured in s) in the visible platform (top) or day 10 probe trial quadrant occupancy (measured in s, bottom) group means±SEM. FIG. 2A depicts combined males and females, FIG. 2B depicts males, FIG. 2C depicts females. *P<0.05, P<0.01, *P<0.001, † a trend of P<0.10 for Tg2576+ vs. Tg2576− groups. FIG. 2D depicts representative low-magnification photomicrographs from Tg2576 or Tg2576/CD11c-DNR mouse brain sections stained as indicated. FIG. 2E depicts Tg2576 (n=12; 5 females and 7 males) or Tg2576/CD11c-DNR (n=10; 7 females and 3 males) mouse brains analyzed for 4G8 (top) or Thioflavin-S "burden" (bottom). "Burden" values (% labeled area, group means±SEM with percentage reduction) are shown on the y-axis and brain region (CC, cingulate cortex; HC, hippocampus; EC, entorhinal cortex) sorted into males and females is shown on the x-axis. † a trend of P<0.10, *P<0.05, P<0.01, *P<0.001, when comparing Tg2576/CD11c-DNR vs. Tg2576 mice within brain region and gender by t-test.

FIGS. 3A-3C, is a series of images and quantitative data demonstrating reduced cerebral parenchymal and vascular β-amyloid deposits in Tg2576-CD11c-DNR mice at 17-18 months of age. FIG. 3A depicts photomicrographs from Tg2576 or Tg2576-CD11c-DNR mouse brain sections with median values by image analysis for human Aβ immunohistochemistry (antibody 4G8, brightfield photomicrographs, left) or histochemistry for thioflavin S (darkfield photomicrographs, right); CC, cingulate cortex; HC, hippocampus; EC, entorhinal cortex. FIG. 3B depicts photomicrographs taken from cortical areas or hippocampus and quantitative image analysis for 4G8 (left) or thioflavin S burden (right) was conducted for Tg2576 (n=12) and Tg2576-CD11c-DNR mice (n=10). 4G8 or thioflavin S burden (% labeled area) is shown on they axis, and brain region is represented on the x axis. Percentage reductions in Tg2576-CD11c-DNR versus littermate Tg2576 mice are indicated for each brain region. FIG. 3C depicts representative photomicrographs of thioflavin S histochemistry (inverted grayscale, left) showing cerebral vascular β-amyloid deposits in Tg2576 or Tg2576-CD11c-DNR mice as indicated (arrows). Semiquantitative image analysis was performed (right), and severity of cerebral amyloid angiopathy (CAA score) is shown on the y axis with brain region indicated on the x axis. Scale bars in (FIGS. 3A and 3C) denote 100 μm. Quantitative data are represented as group means (bars). All statistical comparisons are within brain region and between Tg2576 and Tg2576-CD11c-DNR mice, P<0.01 and *P<0.001.

FIG. 4A-FIG. 4I, is a series of images depicting morphometric and biochemical analysis of Aβ/β-amyloid and APP in Tg2576/CD11c-DNR vs. Tg2576 mouse brains at 17-18 months of age. FIGS. 4A-4C depicts brain sections from Tg2576 (n=12) or Tg2576/CD11c-DNR mice (n=10) reacted with 408 antibody (top row) or thioflavin-S (bottom row), and plaques were counted and assigned to: small (<25 μm; left), medium (from 25 to 50 μm; middle), or large (>50 μm; right) (group means±SEM with percentage reduction). *P<0.05, P<0.01, *P<0.001, when comparing Tg2576/CD11c-DNR vs. Tg2576 mice within brain region by t-test. FIGS. 4D-4F depict two-step extracted brain homogenates assayed for detergent-soluble (FIG. 4D) or 5M guanidine HCl-soluble (FIG. 4E) human $Aβ_{1-40}$ (left), $Aβ_{1-42}$ (middle), or total Aβ (right). $Aβ_{1-42}/Aβ_{1-40}$ ratios are shown in FIG. 4F, ***P<0.001. FIG. 4G depicts Western blots for brain APP and actin (internal loading control), and FIG. 4H depicts blood plasma steady-state $Aβ_{1-40}$ (left) or $Aβ_{1-42}$ (right) levels, FIG. 4I depicts Western blots of detergent-soluble brain homogenates using an APP carboxyl-terminal fragment antibody (Ab) [top; full-length (holo)-APP and APP carboxyl-terminal fragments generated by amyloidogenic (C99) or non-amyloidogenic (C83) cleavage are shown] or antibody 6E10 against the N-terminus of human Aβ (bottom; holo-APP, soluble APP species, and C99 fragments are shown, and actin is a loading control).

FIGS. 5A and 5B depict photomicrographs from Tg2576 (n=12) and Tg2576-CD11c-DNR (n=10) mouse brain sections (FIG. 5A), with median values by image analysis for GFAP immunohistochemistry (FIG. 5B); GFAP burden (% labeled area) is shown on the y axis and brain region is represented on the x axis. FIG. 5C depicts confocal micrographs of Tg2576 or Tg2576-CD11c-DNR brain sections (left, cerebrovessels; right, entorhinal cortex β-amyloid plaques) immunolabeled for human Aβ and mouse CD45 and counterstained with DAPI. Colocalization of Aβ with CD45+ cells in Tg2576-CD11c-DNR mice is denoted by arrows, and some of these cells contain Aβ deposits (high-magnification single optical section insets). FIG. 5D depicts quantitative image analysis for CD45 burden. All statistical comparisons are within brain region and between Tg2576 and Tg2576-CD11c-DNR mice, ***P<0.001, *P<0.05, †P<0.10. FIG. 5E depicts a FACS analysis using fluorescently tagged antibodies to CD45, CD11b and CD11c, as indicated, from five mouse brains per group pooled from double-transgenic Tg(APP,PSEN) mice crossed with CD11c-DNR mice (designated Tg(APP,PSEN)-CD11c-DNR). Logfluorescence intensity for CD45 is indicated on they axis, and forward scatter (FSC, a measure of cell size) is indicated on the x axis. Percentages of cells within each gate are indicated in top plots, and overlays of CD11b and CD11c are shown in bottom plots. Scale bars denote 100 μm (FIG. 5A) and 20 μm (FIG. 5C; 10 μm for insets).

FIGS. 6A-6B, is a series of images depicting age-dependent infiltration of CD11b+CD11c+ macrophage-like cells in Tg2576/CD11c-DNR mouse brains. FIG. 6A depicts brain sections from 17-18 month-old Tg2576 or Tg2576/CD11c-DNR mice (as indicated) immunolabeled with antibodies against CD11b (green signal), CD11c (red signal), or Aβ (4G8, magenta signal) (merged images are shown to the right) and analyzed by laser scanning confocal microscopy. Images in the upper rows were taken from cerebral vessels and images in the lower rows were taken from β-amyloid plaques in the cingulate cortex as indicated. Scale bar denotes 20 μm (calculated for all panels). FIG. 6B depicts brain sections from 12 month-old (12 M) Tg2576 (n=5, 3 females/2 males) and Tg2576/CD11c-DNR mice (n=5, 3 females/2 males) reacted with antibodies against Aβ (4G8, blue signal), CD45 (red signal), or Gfap (green signal), and analyzed by confocal microscopy. Representative images of cingulate cortex from each genotype (as indicated) are shown in the left two columns (scale bar denotes 50 μm), and high-magnification images are shown in the right two columns (scale bar denotes 10 μM, calculated for all panels). Merged images are shown in the bottom row.

FIGS. 7A-7D, is a series of images demonstrating that TGF-β1 shifts CD11c-DNR macrophages from canonical to alternate Smad signaling and increases Aβ phagocytosis in vitro. FIG. 7A depicts primary microglia (MG) or macrophages (MΦ) from wild-type or CD11c-DNR mice when untreated or treated for 30 min with a dose range of recombinant TGF-β1 (1, 5 or 10 ng/ml as indicated) with or without 50 ng/ml of LPS. Cell lysates were western blotted for phosphorylated (p) and total Smad2/3 proteins as an indicator of canonical TGF-β-activated signaling. FIG. 7B depicts primary macrophages treated as above and western blotted for phosphorylated and total Smad1/5/8 or p21-activated kinase 2 (Pak2; both activated in the alternate Smad signaling pathway triggered by bone morphogenic protein stimulation), or extracellular signal-regulated kinase (Erk) 1/2. FIG. 7C depicts primary macrophages pulsed for 4 h with 2 μg/ml of preaggregated $Aβ_{488}$ and chased for 15 min before analysis by confocal microscopy with antibodies to CD11b or CD11c (merged images are shown on the right). FIG. 7D depicts quantification of confocal images (n=3 randomly-selected fields per group), and Aβ488-labeled area is shown on the left. Numbers of Aβ488 phagocytic cells per field are shown in the middle graph. Data are represented as group means±s.d. Cell lysates were prepared from macrophages treated in parallel with 2 μg/ml of unlabeled human synthetic $Aβ_{1-42}$, and 2 ng of the peptide (cell-free) was western blotted side-by-side with antibody 6E10 (right). Data shown in FIGS.

7A-7D are representative of three to four independent experiments in which similar results were obtained.

Figure 8:
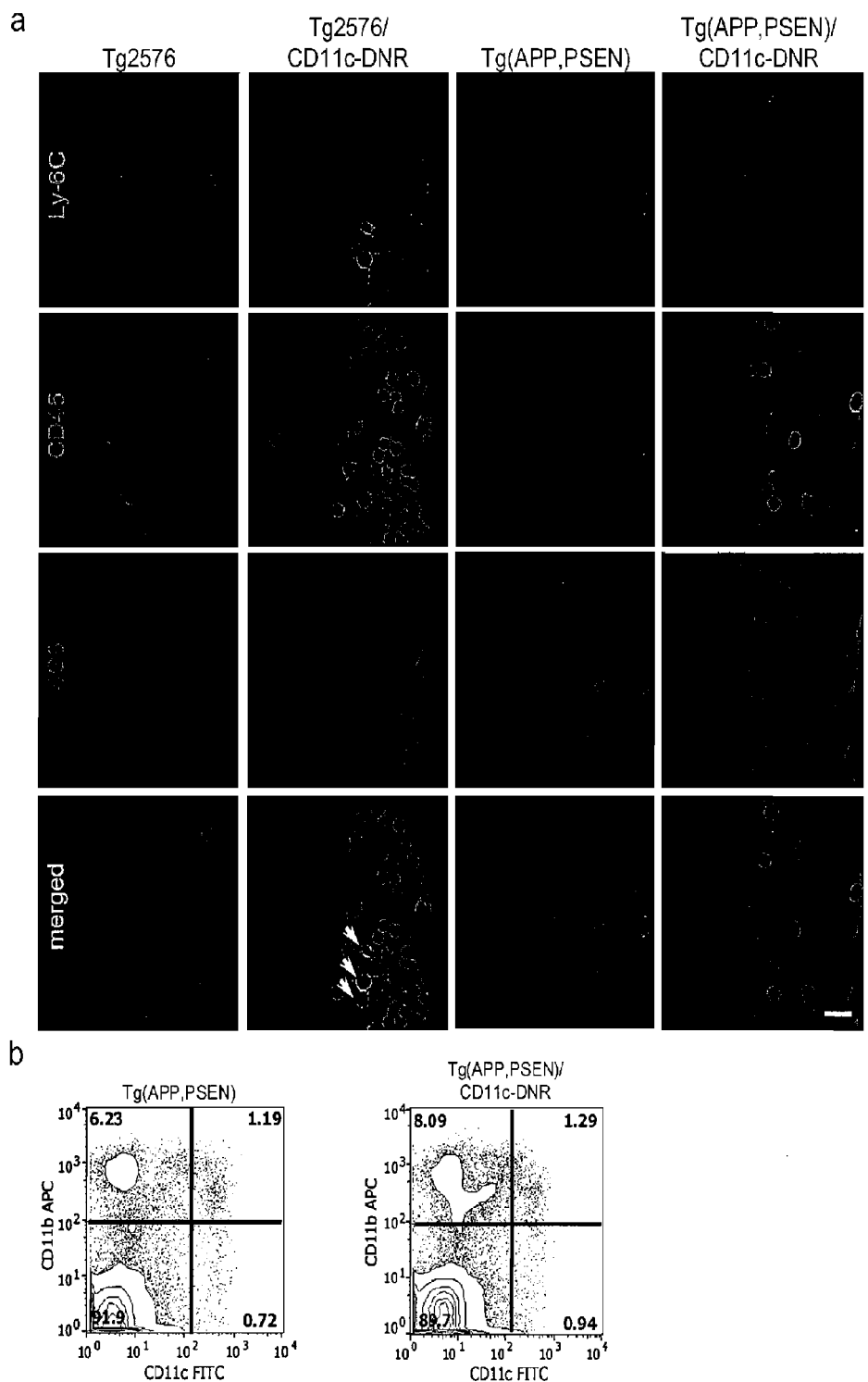

FIG. 8, comprising FIGS. 8A and 8B, is a series of images depicting levels of peripheral and CNS macrophages in AD and crossed mice. FIG. 8A depicts brain sections from Tg2576 and Tg2576/CD11c-DNR mice at 17-18 months of age, or Tg(APP,PSEN) and Tg(APP,PSEN)/CD11c-DNR mice at 15 months of age reacted with antibodies against Ly-6C (green signal), CD45 (red signal), or Aβ (4G8 antibody, blue signal), and confocal images are shown of cerebral vessels in the entorhinal cortex. Merged images are shown in the bottom row, and arrowheads indicate cells double-positive for Ly-6C and CD45. Seale bar denotes 10 μm. FIG. 8B depicts FACS dot-plots showing similar levels of peripheral CD11b+CD11c+ cells isolated from spleens of Tg(APP,PSEN) and Tg(APP,PSEN)/CD11c-DNR mice at 15 months of age.

Figure 9:
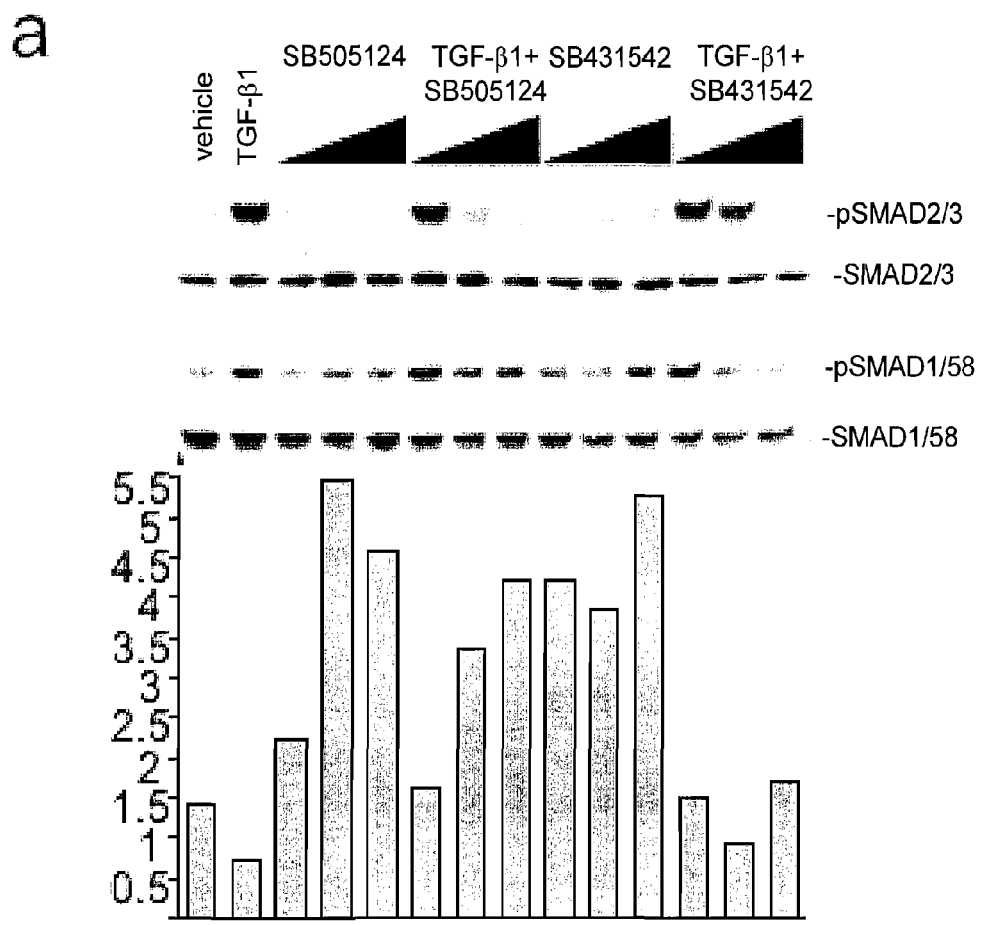
Figure 9:
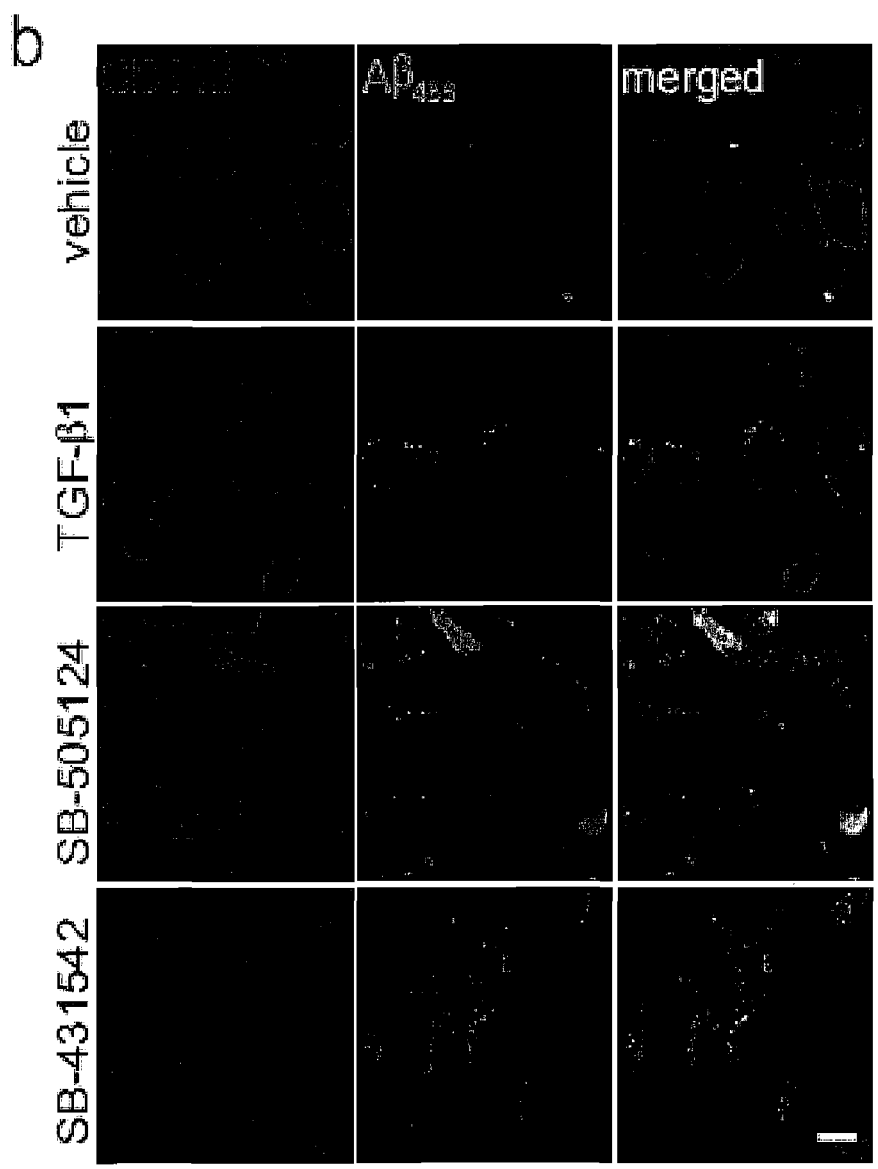
Figure 9:
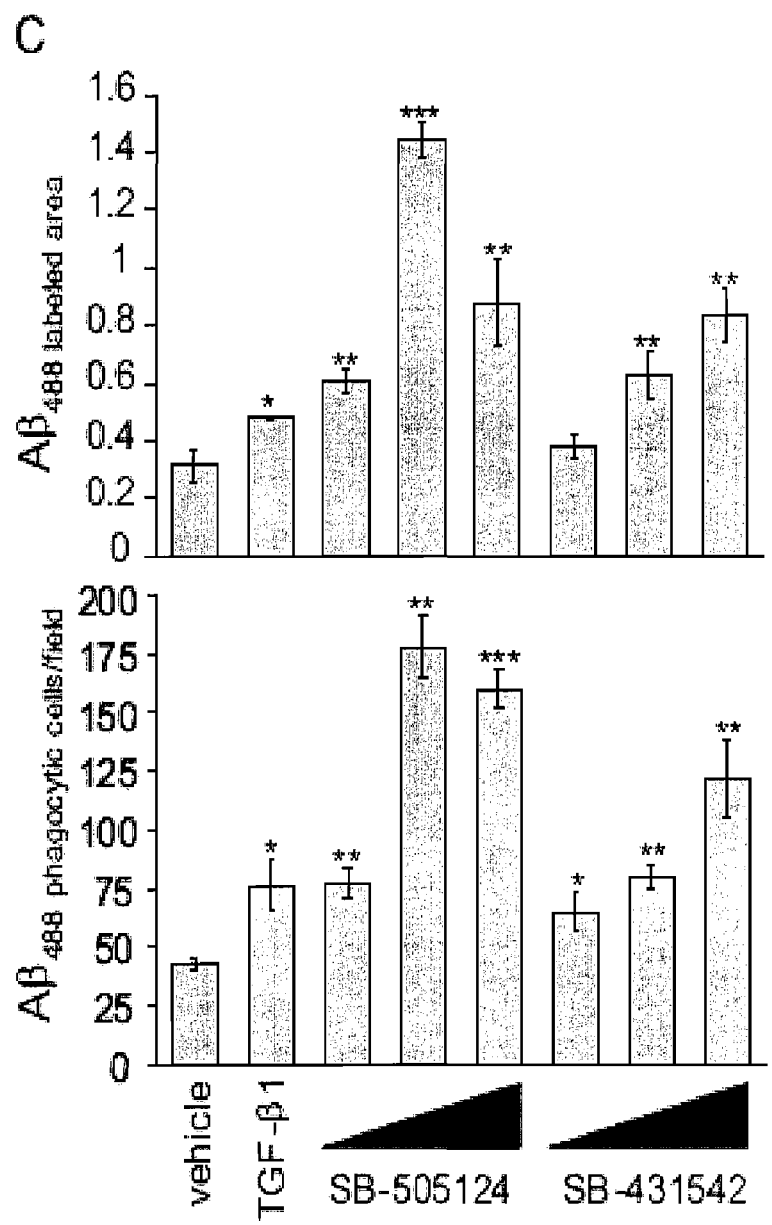
Figure 9:
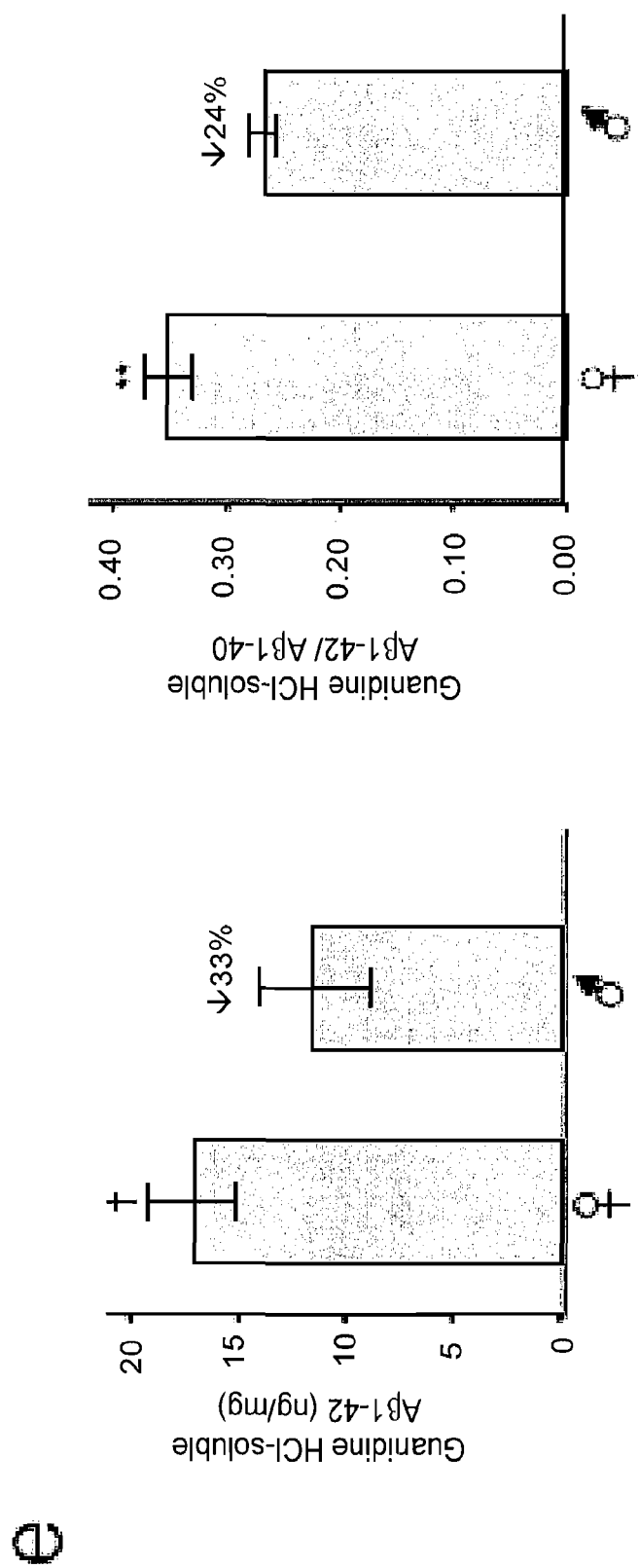
Figure 9:
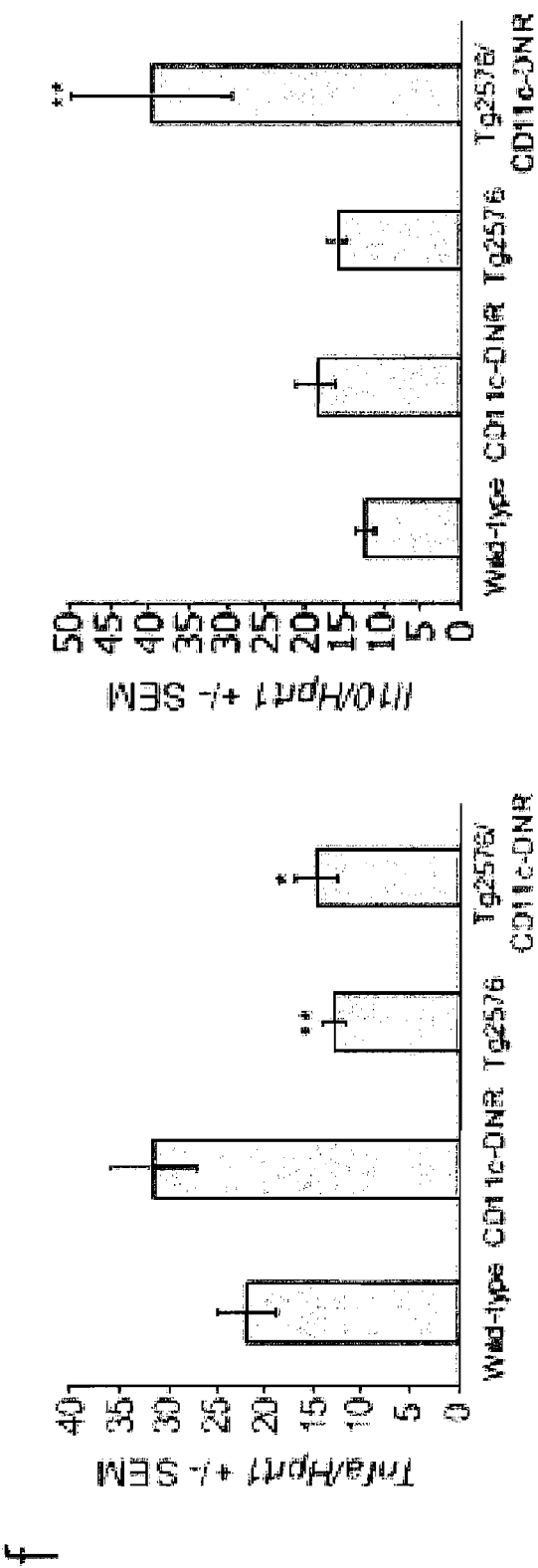

FIG. 9, comprising FIGS. 9A-9F, is a series of images depicting Activin-like kinase (ALK) inhibition increases the ratio of phospho-SMAD1/5/8 to phospho-SMAD2/3 and promotes macrophage Aβ phagocytosis. FIG. 9A depicts peripheral MΦ pre-treated with a dose range (0.1, 1.0, or 10.0 μM) of ALK5 inhibitors (SB-505124 or SB-431542) for 1 h and then cultured in the presence or absence of recombinant TGF-β1 (5 ng/mL) for 30 min as indicated. Upper panels show Western blots for phospho (p) or total forms of SMAD2/3 or SMAD1/5/8. Lower panel is a histogram showing the ratio of pSMAD1/5/8 to pSMAD2/3. FIG. 9B depicts representative confocal images of primary MΦ cultured in the presence or absence of TGF-β1 or ALK5 inhibitors for 1 h, pulsed for 4 h with 2 μg/mL "pre-aggregated" HiLyte Fluor™ 488-labeled Aβ$_{1-42}$ (Aβ488), and chased for 15 min prior to analysis by laser scanning confocal microscopy in conjunction with CD11b (red signal) antibody (merged images are shown in the right panels, images are from a 1.0 μM ALK5 inhibitor dose). FIG. 9C depicts quantification of confocal images (n=3 randomly selected 10× magnification fields per group, group means±s.d.), and Aβ488-labeled area is shown in the upper graph, and numbers of Aβ488 phagocytic cells/field are shown in the lower graph. FIGS. 9D-9F depict gender-dependent reductions in Aβ levels in Tg2576+ animals and anti-inflammatory responses in brains of crossed mice. Biochemical analyses of (FIG. 9D) detergent-soluble and (FIG. 9E) guanidine HCl-soluble Aβ$_{1-42}$ and Aβ$_{1-42}$/Aβ$_{1-40}$ in male vs. female Tg2576 positive mice (irrespective of CD11c-DNR transgene status). FIG. 9F depicts Q-PCR results for Tnfa (left) or Il10 (right) expression (relative to Hprt1) shown for four groups of mice, and statistical comparisons vs. wild-type mice. For FIGS. 9C-9F, † a trend of $P<0.10$, *$P<0.05$, $P<0.01$, *$P<0.001$.

FIG. 10 is a chart depicting ANOVA results for behavioral testing. Multiple ANOVA models were designed with gender, genotype, and (where appropriate) time as covariates. Genotype was coded as three groups (including combined wild-type and CD11c-DNR mice as controls, Tg2576 mice, or Tg2576/CD11c-DNR mice) or two groups (Tg2576 positive or Tg2576 negative mice). Main effects and interactive terms are shown for each behavioral measure. Stratification by gender produced similar trends in both males and females (data not shown).

FIG. 11 is a chart depicting semi-quantitative histology results for CD45+CD11b+ infiltrating MΦ in individual Tg(APP,PSEN) or Tg(APP,PSEN)/CD11c-DNR mice at 15 months of age. Brain sections (4 per mouse, spaced 50 μm apart) from individual Tg(APP,PSEN) or Tg(APP,PSEN)/CD11c-DNR mice were immunostained with antibodies against CD45 and CD11b and cortical areas and hippocampus were scored on a five-point semi-quantitative scale for presence of infiltrating MΦ. Mouse identification (ID) numbers are shown in the left column, mouse genotypes (formatted as Tg(APP,PSEN)/CD11c-DNR) are shown in the middle column, and average scores from each set of sections per mouse are shown in the right column. Scoring was as follows: (−), absence of cells; (+/−), very few cells present; (+) cells mildly present; (++), cells moderately present; (+++), cells present in large quantity; $P<0.01$ when comparing +/+ to +/− mouse groups.

Figure 12:
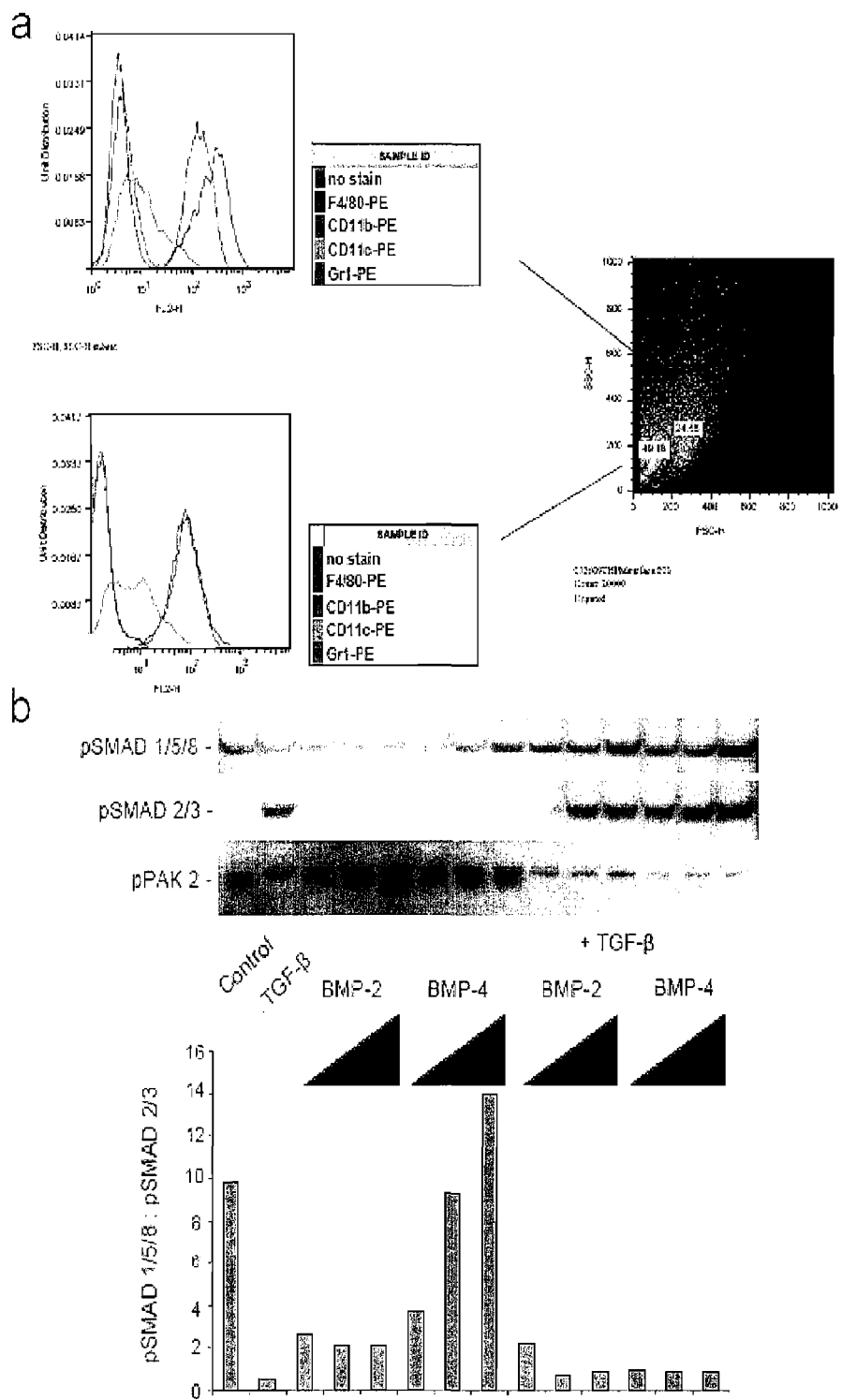
Figure 12:
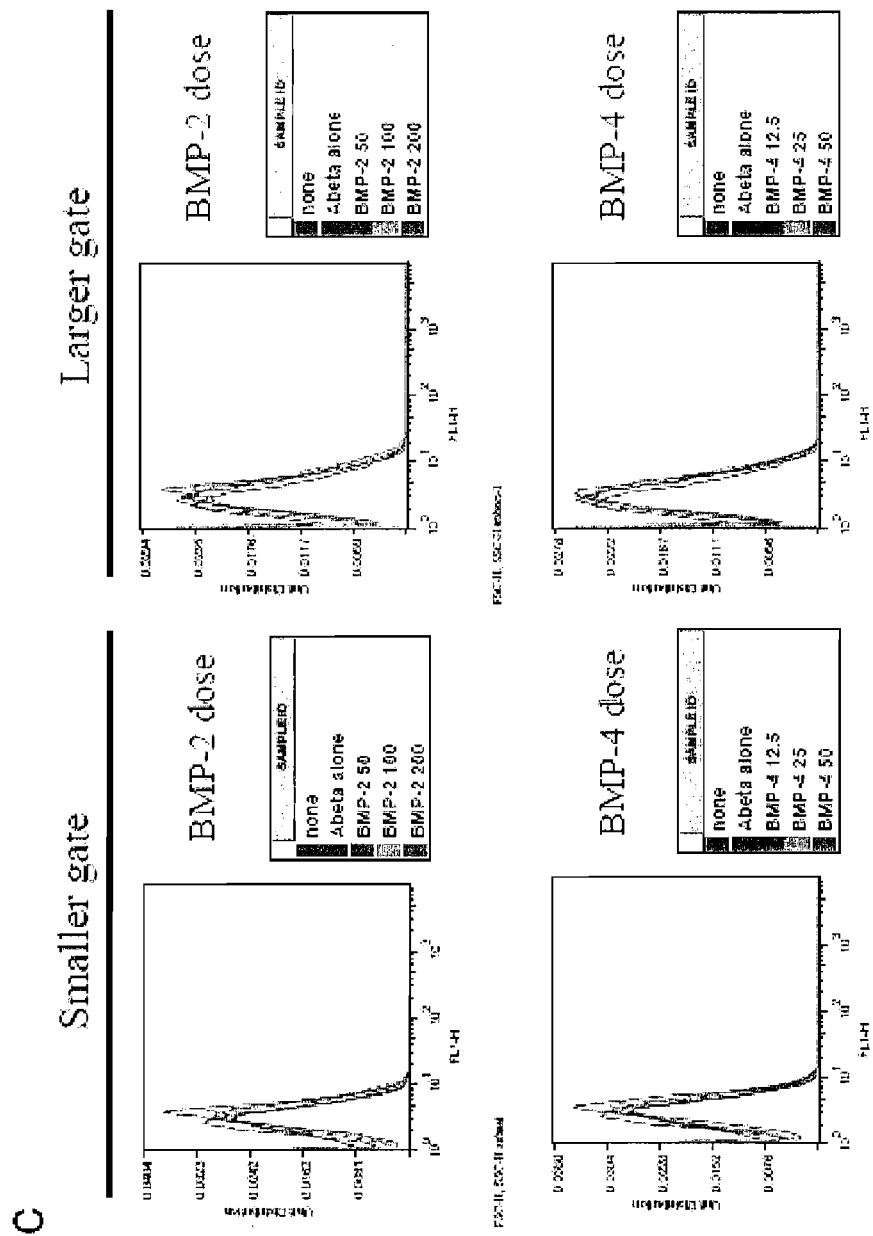

FIG. 12, comprising FIGS. 12A-12C, is a series of images depicting isolation of peripheral macrophages from C57BL/6 wild-type mice and the effects of BMP and/or TGF-β1 recombinant protein addition to these macrophages on Smad 2/3, Smad 1/5/8, and p21-activated kinase 2 (PAK2) activation and Aβ phagocytosis and clearance. FIG. 12A depicts flow cytometry results showing expression of the innate immune cell/macrophage markers F4/80 antigen, CD11b, and CD11c in two gated populations of isolated peripheral macrophages. FIG. 12B depicts western blots showing phosphorylated (p; activated) forms of Smad1/5/8, Smad2/3, and PAK2 (another component of the Smad1/5/8 signaling pathway) without treatment (control), or 30 minutes after treatment with TGF-β1 (5 ng/mL) in the presence or absence of a dose range of recombinant BMP-2 (50, 100, or 200 ng/mL) or recombinant BMP-4 (12.5, 25, or 50 ng/mL). The ratio of phosphorylated Smad1/5/8 to phosphorylated Smad2/3 is shown below the western blots. FIG. 12C depicts flow cytometry results showing results from two gates (smaller or larger gates, as indicated) of macrophages left untreated (none) or pre-treated for 1 hour with a dose-range of recombinant BMP-2 (50, 100, or 200 ng/mL) or recombinant BMP-4 (12.5, 25, or 50 ng/mL). Macrophages were then pulsed for 3 h with 1 μg/mL of "pre-aggregated" HiLyte Fluor™ 488-labeled Aβ$_{1-42}$ (Aβ488), and chased for 15 min prior to analysis by flow cytometry for Aβ488. Note the increase in Aβ488 internalization at the 50 ng/mL dose of BMP-2 and at the 12.5 ng/mL dose of BMP-4.

DETAILED DESCRIPTION OF THE INVENTION

The present invention encompasses compositions and methods for treating Alzheimer's disease by interfering with TGF-β signaling in innate immune cells, preferably but not limited to peripheral macrophages, wherein the peripheral macrophages are able to infiltrate into the central nervous system (CNS) to improve amyloid-β peptide (Aβ) clearance. The present invention is based on the discovery that inhibition of TGF-β signaling in peripheral macrophages increases Aβ phagocytosis when the macrophages are present in the diseased CNS tissue.

In some instances, the invention includes interfering with TFG-β and downstream Smad 2/3 signaling in peripheral macrophages to increase Aβ phagocytosis. In other instances, the invention also includes activating bone morphogenic protein (BMP)-activated Smad 1/5/8 signaling in peripheral macrophages to increase Aβ phagocytosis.

Using the methods disclosed elsewhere herein, the skilled artisan can readily increase clearance of cerebral Aβ in a diseased CNS tissue by blocking at least TGF-β signaling in peripheral macrophages. TGF-β inhibited macrophages can lead to en masse brain infiltration and beneficial cerebral Aβ clearance. Thus, inhibition of at least TGF-β signaling on peripheral macrophages represents an advantageous anti-amyloid therapeutic approach for Alzheimer's disease. The methods of the invention are contemplated for use in a mammal, preferably, a human.

Based on the disclosure presented herein, a skilled artisan would appreciate that interfering with TFG-β and downstream Smad 2/3 signaling in peripheral macrophages is also useful as an anti-amyloid therapy. Furthermore, a skilled artisan would appreciate that activating bone morphogenic protein (BMP)-activated Smad 1/5/8 signaling in peripheral macrophages to increase Aβ phagocytosis is useful as an anti-amyloid therapy.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Allogeneic" refers to a graft derived from a different animal of the same species.

"Alloantigen" is an antigen that differs from an antigen expressed by the recipient.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "β-amyloid, amyloid-β, and/or amyloid peptide" as used herein, encompasses monomeric, oligomeric, and/or fibrillar forms of β-amyloid in water-soluble or water-insoluble states, or any fibril protein as discussed herein, as well as any other structural variants that may occur naturally, are synthetically constructed or correspond to a known fibril protein.

The term "amyloid related diseases" includes diseases associated with the accumulation of amyloid which can either be restricted to one organ, "localized amyloidosis", or spread to several organs, "systemic amyloidosis". Secondary amyloidosis may be associated with chronic infection (such as tuberculosis) or chronic inflammation (such as rheumatoid arthritis), including a familial form of secondary amyloidosis which is also seen in Familial Mediterranean Fever (FMF) and another type of systemic amyloidosis found in long-term hemodialysis patients. Localized forms of amyloidosis include, without limitation, diabetes type II and any related disorders thereof, neurodegenerative diseases such as scrapie, bovine spongiform encephalitis, Creutzfeldt-Jakob disease, Alzheimer's disease, Cerebral Amyloid Angiopathy, and prion protein related disorders.

The terms "Aβ," "Aβ peptide" and "Amyloid-β" peptide are synonymous, and refer to one or more peptide compositions of about 38-43 amino acids derived from Beta Amyloid Precursor Protein (β-APP), as described herein. Disaggregated Aβ means soluble, monomeric and oligomeric peptide units of Aβ. One method to prepare monomeric Aβ is to dissolve lyophilized peptide in neat DMSO with sonication. The resulting solution is centrifuged to remove any insoluble particulates. Aggregated Aβ is a mixture of oligomers in which the monomeric units are held together by noncovalent bonds. Furthermore, APP695, APP751, and APP770 refer, respectively, to the 695, 751, and 770 amino acid residue long polypeptides encoded by the human APP gene. See Kang et al., Nature 325, 773 (1987); Ponte et al., Nature 331, 525 (1988); and Kitaguchi et al., Nature 331, 530 (1988). Amino acids within the human amyloid precursor protein (APP) are assigned numbers according to the sequence of the APP770 isoform. Terms such as Aβ39, Aβ40, Aβ41, Aβ42 and Aβ43 refer to an Aβ peptide containing amino acid residues 1-39, 1-40, 1-41, 1-42 and 1-43.

As used herein, the term a "sensitized marcrophage" or a "sensitized peripheral marcrophage" refers to a macrophage or monocyte, which has been exposed to an agent that inhibits TGF-β and/or TGF-β and downstream Smad 2/3 signaling in the macrophage or monocyte. A "sensitized marcrophage" or a "sensitized peripheral marcrophage" also refers to a macrophage or monocyte, which has been exposed to an agent that activates bone morphogenic protein (BMP)-activated Smad 1/5/8 signaling in the macrophage or monocyte. The "sensitized marcrophage" or a "sensitized peripheral marcrophage" has 1) increased penetration into the central nervous system and/or 2) an increased amyloid-β peptide (Aβ) phagocytic activity compared to an otherwise identical macrophage that has not been sensitized.

"Antisense" refers particularly to the nucleic acid sequence of the non-coding strand of a double stranded DNA molecule encoding a polypeptide, or to a sequence which is substantially homologous to the non-coding strand. As defined herein, an antisense sequence is complementary to the sequence of a double stranded DNA molecule encoding a polypeptide. It is not necessary that the antisense sequence be complementary solely to the coding portion of the coding strand of the DNA molecule. The antisense sequence may be complementary to regulatory sequences specified on the coding strand of a DNA molecule encoding a polypeptide, which regulatory sequences control expression of the coding sequences.

As used herein, the term "autologous" is meant to refer to any material derived from the same individual to which it is later to be re-introduced into the individual.

The term "DNA" as used herein is defined as deoxyribonucleic acid.

"Donor antigen" refers to an antigen expressed by the donor tissue to be transplanted into the recipient.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Roth the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, microRNA, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "heterologous" as used herein is defined as DNA or RNA sequences or proteins that are derived from the different species.

"Homologous" as used herein, refers to the subunit sequence similarity between two polymeric molecules, e.g., between two nucleic acid molecules, e.g., two is DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 5'ATTGCC3' and 5'TATGGC3' share 50% homology.

As used herein, "homology" is used synonymously with "identity."

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence. It also includes a nucleic acid that have been removed from its native environment and placed in another, typically artificial, environment.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the term "modulate" is meant to refer to any change in biological state, i.e. increasing, decreasing, and the like. For example, the term "modulate" refers to the ability to regulate positively or negatively the expression or activity of TGF-β and/or downstream Smad 2/3 signaling in a macrophage or monocyte. In some instances, the term "modulate" refers to the ability to regulate positively or negatively the expression or activity of bone morphogenic protein (BMP)-Smad 1/5/8 signaling in a macrophage or monocyte.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein".

"Proliferation" is used herein to refer to the reproduction or multiplication of similar forms of entities, for example proliferation of a cell. That is, proliferation encompasses production of a greater number of cells, and can be measured by, among other things, simply counting the numbers of cells, measuring incorporation of $^3$H-thymidine into the cell, and the like.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

"Fragment" as the term is used herein, is a nucleic acid sequence that differs in length (i.e., in the number of nucleotides) from the length of a reference nucleic acid sequence, but retains essential properties of the reference molecule. Similarly, a protein fragment can exist that is a part of a larger parent protein. One example of a retained essential property would be the ability of the fragment nucleic acid to hybridize to a particular target mRNA, much like the reference nucleic acid sequence, and thereby diminish expression. A fragment of a nucleic acid can be a naturally occurring or can be a fragment that is not known to occur naturally. Non-naturally occurring fragments of nucleic acids may be made by mutagenesis techniques or by direct synthesis. Preferably, the fragment is at least about 25% of the length of the reference nucleic acid sequence. More preferably, the fragment is at least about 35% of the length of the reference nucleic acid sequence. Even more preferably, the fragment is at least about 45% of the length of the reference nucleic acid sequence.

"Variant" as the term is used herein, is a nucleic acid sequence that differs in sequence from a reference nucleic acid sequence, but retains essential properties of the reference molecule. One example of a retained essential property would be the ability of the variant nucleic acid to hybridize to a particular target mRNA, much like the reference nucleic acid sequence, and thereby diminish expression. A variant of a nucleic acid can be a naturally occurring such as an allelic variant, or can be a variant that is not known to occur naturally. Non-naturally occurring variants of nucleic acids may be made by mutagenesis techniques or by direct synthesis. Preferably, the variant shares at least about 80% homology with the reference nucleic acid sequence. More preferably, the variant shares at least about 90% homology with the reference nucleic acid sequence. Even more preferably, the variant shares at least about 95% homology with the reference nucleic acid sequence.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "T-cell" as used herein is defined as a thymus-derived cell that participates in a variety of cell-mediated immune reactions.

The term "B-cell" as used herein is defined as a cell derived from the bone marrow and/or spleen. B cells can develop into plasma cells which produce antibodies.

The terms "macrophage" or "monocyte" are herein defined as cells derived from the bone marrow and/or spleen that are capable of internalizing proteins, bacteria, and/or viruses and neutralizing these stated substances. These cells can be tissue-resident, for example "microglia" in the brain, and can also be present systemically, such as blood monocytes.

As used herein, a "therapeutically effective amount" is the amount of a therapeutic composition sufficient to provide a beneficial effect to a mammal to which the composition is administered.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "virus" as used herein is defined as a particle consisting of nucleic acid (RNA or DNA) enclosed in a protein coat, with or without an outer lipid envelope, which is capable of replicating within a whole cell.

"Xenogeneic" refers to a graft derived from an animal of a different species.

A "conservative substitution" is the substitution of an amino acid with another amino acid with similar physical and chemical properties. In contrast, a "nonconservative substitution" is the substitution of an amino acid with another amino acid with dissimilar physical and chemical properties.

As used herein, the terms "gene" and "recombinant gene" refer to nucleic acid molecules comprising an open reading frame encoding a polypeptide.

As used herein, the term "genetically engineered" refers to a modification of the inherent genetic material of a microorganism (e.g., one or more of the deletion such as a gene knockout, addition, or mutation of one or more nucleic acid residues within the genetic material), addition of exogenous genetic material to a microorganism (e.g., transgene, stable plasmid, integrating plasmid, naked genetic material, among other things), causing the microorganism to alter its genetic response due to external or internal signaling (e.g., environmental pressures, chemical pressures, among other things), or any combination of these or similar techniques for altering the overall genetic makeup of the organism.

"Mutants," "derivatives," and "variants" of a polypeptide (or of the DNA encoding the same) are polypeptides which may be modified or altered in one or more amino acids (or in one or more nucleotides) such that the peptide (or the nucleic acid) is not identical to the wild-type sequence, but has homology to the wild type polypeptide (or the nucleic acid).

A "mutation" of a polypeptide (or of the DNA encoding the same) is a modification or alteration of one or more amino acids (or in one or more nucleotides) such that the peptide (or nucleic acid) is not identical to the sequences recited herein, but has homology to the wild type polypeptide (or the nucleic acid).

As used herein, a "mutant form" of a gene is a gene which has been altered, either naturally or artificially, changing the base sequence of the gene, which results in a change in the amino acid sequence of an encoded polypeptide. The change in the base sequence may be of several different types, including changes of one or more bases for different bases, small deletions, and small insertions. Mutations may also include transposon insertions that lead to attenuated activity, i.e., by resulting in expression of a truncated protein, By contrast, a normal form of a gene is a form commonly found in a natural population of an organism, Commonly a single form of a gene will predominate in natural populations. In general, such a gene is suitable as a normal form of a gene; however, other forms which provide similar functional characteristics may also be used as a normal gene.

The term "engineer" refers to any manipulation of a cell that result in a detectable change in the cell, wherein the manipulation includes but is not limited to inserting a polynucleotide and/or polypeptide heterologous to the cell and mutating a polynucleotide and/or polypeptide native to the cell. A polynucleotide or polypeptide is "heterologous" to a cell if it is not part of the polynucleotides and polypeptides expressed in the cell as it exists in nature, i.e., it is not part of the wild-type of that cell. A polynucleotide or polypeptide is instead "native" to a cell if it is part of the polynucleotides and polypeptides expressed in the cell as it exists in nature, i.e., it is part of the wild-type of that cell.

Description

A variety of components of the TGF-β and downstream signaling system can serve as targets for inhibition in a macrophage in order to increase the ability of the macrophage to penetrate the central nervous system and phagocytosize and clear Aβ. In addition, components of the bone morphogenic protein-Smad1/5/8 signaling pathway can serve as targets for activation in a macrophage to increase the ability of the macrophage to penetrate the central nervous system and phagocytosize and clear Aβ.

Thus, the invention encompasses inhibiting TGF-β-Smad2/3 signaling in peripheral macrophages as a therapeutic target for Alzheimer's disease. In some instances, the invention includes activating Smad1/5/8 signaling in macrophages as a therapeutic target for treating Alzheimer's disease. In some instances, the act of blocking Smad2/3 signaling results in promotion of Smad1/5/8 signaling, which is associated with increased macrophage Aβ phagocytosis. In other instances, the invention encompasses any combination of inhibiting TGF-β, TGF-β-Smad2/3 signaling, and activating bone morphogenie protein-Smad1/5/8 signaling pathway.

The invention provides compositions and methods for regulating the TGF-β signaling system. In one embodiment, the invention relates to regulating TGF-β β and down stream Smad 2/3 signaling. In another embodiment, the invention relates to regulating TGF-β and down stream signaling as well as the bone morphogenic protein-Smad1/5/8 signaling pathway. In another embodiment, the invention relates to regulating bone morphogenic protein-Smad1/5/8 signaling pathway. In yet another embodiment, the invention relates to regulating any combination at of TGF-β, TGF-β down stream signaling, and bone morphogenic protein-Smad1/5/8 signaling pathway.

The invention is based on the discovery that inhibiting TGF-β and therefore TGF-β down stream signaling in peripheral macrophages serves to increase macrophage Aβ phagocytosis activity. The invention is also based on the discovery that inhibiting TGF-β and therefore TGF-β down stream signaling in peripheral macrophages also results in promotion of Smad1/5/8 signaling, which is associated with increasing macrophage Aβ phagocytosis activity. In addition, the invention is based on the discovery that direct addition of bone morphogenic proteins results in promotion of Smad1/5/8 signaling and increased macrophage Aβ phagocytosis activity. Thus, the present invention provides an Alzheimer's therapy comprising inhibiting at least TGF-β signaling in peripheral macrophages to promote increased brain infiltration of blood-derived macrophages and Aβ clearance in an Alzheimer's brain tissue. In addition, the present invention provides a therapeutic benefit for inhibiting at least TGF-β signaling in the treatment of diseases or disorders associated with increased levels of Aβ.

Inhibitor of TGF-β

Based on the disclosure herein, the present invention includes a generic concept for inhibiting TGF-β or TGF-β signaling pathway in peripheral macrophages to promote brain infiltration of blood-derived macrophages and Aβ clearance when the infiltrated macrophages are present in the CNS of a mammal suffering from Alzheimer's disease.

In one embodiment, the invention comprises a composition for enhancing the ability of an innate immune cell, preferably a peripheral macrophage or monocyte, to phagocytosize Aβ. The composition comprises an inhibitor of one or more of the following: TGF-β or TGF-β down stream signaling pathway in a peripheral macrophage. Thus, as referred to herein, inhibiting TGF-β can also encompass inhibiting any component of the TGF-β signaling pathway, such as activin-like kinase 5 (ALK5, a key TGF-β receptor I that pairs with TGF-β receptor II for signaling).

The composition comprising the inhibitor of a component of the TGF-β signaling pathway can be any type of inhibitor. For example and without limitation, the inhibitor can be selected from the group consisting of a small interfering RNA (siRNA), a microRNA, an antisense nucleic acid, a ribozyme, an expression vector encoding a transdominant negative mutant, an intracellular antibody, a peptide and a small molecule.

As disclosed herein, the inhibition of a component of the TGF-β signaling pathway in a macrophage increases the macrophage's Aβ phagocytosis activity. These effects are mediated through inhibition of TGF-β signaling pathway. One skilled in the art will appreciate, based on the disclosure provided herein, that one way to decrease the mRNA and/or protein levels of a component of the TGF-β signaling pathway in a cell is by reducing or inhibiting expression of the nucleic acid encoding a desired component of the TGF-β signaling pathway. Thus, the protein level of the component of the TGF-β signaling pathway in a cell can also be decreased using a molecule or compound that inhibits or reduces gene expression such as, for example, an antisense molecule or a ribozyme.

By way of a non-limited example, inhibition of a component of TGF-β signaling pathway is described below in the context of decreasing the mRNA and/or protein levels of a component of the TGF-β signaling pathway in a cell by reducing or inhibiting expression of the nucleic acid encoding a desired component of the TGF-β signaling pathway.

In a preferred embodiment, the modulating sequence is an antisense nucleic acid sequence which is expressed by a plasmid vector. The antisense expressing vector is used to transfect a mammalian cell or the mammal itself, thereby causing reduced endogenous expression of a desired component of the TGF-β signaling pathway in the cell. However, the invention should not be construed to be limited to inhibiting expression of a component of the TGF-β signaling pathway by transfection of cells with antisense molecules. Rather, the invention encompasses other methods known in the art for inhibiting expression or activity of a protein in the cell including, but not limited to, the use of a ribozyme, the expression of a non-functional component of the TGF-β signaling pathway (i.e. transdominant negative mutant) and use of an intracellular antibody.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262: 40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

The ability to specifically inhibit gene function in a variety of organisms utilizing antisense RNA or dsRNA-mediated interference (RNAi or dsRNA) is well known in the fields of molecular biology. dsRNA (RNAi) typically comprises a polynucleotide sequence identical or homologous to a target gene (or fragment thereof) linked directly, or indirectly, to a polynucleotide sequence complementary to the sequence of the target gene (or fragment thereof). The dsRNA may comprise a polynucleotide linker sequence of sufficient length to allow for the two polynucleotide sequences to fold over and hybridize to each other; however, a linker sequence is not necessary. The linker sequence is designed to separate the antisense and sense strands of RNAi significantly enough to limit the effects of steric hindrances and allow for the formation of dsRNA molecules and should not hybridize with sequences within the hybridizing portions of the dsRNA molecule. The specificity of this gene silencing mechanism appears to be extremely high, blocking expression only of targeted genes, while leaving other genes unaffected. Accordingly, one method for treating Alzheimer's disease according to the invention comprises the use of materials and methods utilizing double-stranded interfering RNA (dsRNAi), or RNA-mediated interference (RNAi) comprising polynucleotide sequences identical or homologous to a desired component of TGF-β signaling pathway. The terms "dsRNAi", "RNAi", "iRNA", and "siRNA" are used interchangeably herein unless otherwise noted.

RNA containing a nucleotide sequence identical to a fragment of the target gene is preferred for inhibition; however, RNA sequences with insertions, deletions, and point mutations relative to the target sequence can also be used for inhibition. Sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Alternatively, the duplex region of the RNA may be defined functionally as a nucleotide sequence that is capable of hybridizing with a fragment of the target gene transcript.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands); the promoters may be known inducible promoters such as baculovirus. Inhibition may be targeted by specific transcription in an organ, tissue, or cell type. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in the art (see, for example, WO 97/32016; U.S. Pat. Nos. 5,593, 874; 5,698,425; 5,712,135; 5,789,214; and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no, or a minimum of, purification to avoid losses due to sample processing. The RNA may be dried for storage or dissolved in an aqueous solution. The solution may contain buffers or salts to promote annealing, and/or stabilization of the duplex strands.

Fragments of genes can also be utilized for targeted suppression of gene expression. These fragments are typically in the approximate size range of about 20 consecutive nucleotides of a target sequence. Thus, targeted fragments are preferably at least about 15 consecutive nucleotides. In certain embodiments, the gene fragment targeted by the RNAi molecule is about 20-25 consecutive nucleotides in length. In a more preferred embodiment, the gene fragments are at least about 25 consecutive nucleotides in length. In an even more preferred embodiment, the gene fragments are at least 50 consecutive nucleotides in length. Various embodiments also allow for the joining of one or more gene fragments of at least about 15 nucleotides via linkers. Thus, RNAi molecules useful in the practice of the instant invention can contain any number of gene fragments joined by linker sequences.

In yet other embodiments, the gene fragments can range from one nucleotide less than the full-length gene. Nucleotide sequences for TGF-β and components of TGF-β signaling pathway are known in the art and can be obtained from patent publications, public databases containing nucleic acid sequences, or commercial vendors. A skilled artisan would understand that the disclosure presented herein provides sufficient written support for any fragment length ranging from about 15 consecutive polynucleotides to one nucleotide less than the full length polynucleotide sequence of TGF-β and components of TGF-β signaling pathway can have a whole number value ranging from about 15 consecutive nucleotides to one nucleotide less than the full length polynucleotide.

Accordingly, methods utilizing RNAi molecules in the practice of the subject invention are not limited to those that are targeted to the full-length polynucleotide or gene. Gene product can be inhibited with an RNAi molecule that is targeted to a portion or fragment of the exemplified polynucleotides; high homology (90-95%) or greater identity is also preferred, but not essential, for such applications.

In another aspect of the invention, the dsRNA molecules of the invention may be introduced into cells with single stranded (ss) RNA molecules which are sense or anti-sense RNA derived from the nucleotide sequences disclosed herein. Methods of introducing ssRNA and dsRNA molecules into cells are well-known to the skilled artisan and includes transcription of plasmids, vectors, or genetic constructs encoding the ssRNA or dsRNA molecules according to this aspect of the invention; electroporation, biolistics, or other well-known methods of introducing nucleic acids into cells may also be used to introduce the ssRNA and dsRNA molecules of this invention into cells.

Other types of gene inhibition can be used to inhibit TGF-β and/or components of TGF-β signaling pathway in a cell. Ribozymes and their use for inhibiting gene expression are also well known in the art (see, e.g., Ceeh et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053). Ribozymes are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, S. Amer. Med. Assn. 260:3030), A major advantage of this approach is the fact that ribozymes are sequence-specific.

There are two basic types of ribozymes, namely, tetralaymeria-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of a component of TGF-β signaling pathway may be designed by incorporating target sequences into the basic ribozyme structure which are complementary to the mRNA sequence of the desired component of TGF-β signaling pathway of the present invention. Ribozymes targeting the desired component of TGF-β signaling pathway may be synthesized using commercially available reagents (Applied Biosystems, Inc., Foster City, Calif.) or they may be genetically expressed from DNA encoding them.

In another aspect of the invention, the component of the TGF-β signaling pathway can be inhibited by way of inactivating and/or sequestering the desired component of the TGF-β signaling pathway. As such, inhibiting the effects of a component of the TGF-β signaling pathway can be accomplished by using a transdominant negative mutant. Alternatively an intracellular antibody specific for the desired component of the TGF-β signaling pathway, otherwise known as an antagonist to the component of the TGF-β signaling pathway may be used. In one embodiment, the antagonist is a protein and/or compound having the desirable property of interacting with a binding partner of the component of the TGF-β signaling pathway and thereby competing with the corresponding wild-type component of the TGF-β signaling pathway. In another embodiment, the antagonist is a protein and/or compound having the desirable property of interacting with the component of the TGF-β signaling pathway and thereby sequestering the component of the TGF-β signaling pathway.

By way of a non-limited example, an antibody is described below as an example of inactivating and/or sequestering the desired component of the TGF-β signaling pathway.

Antibodies

As will be understood by one skilled in the art, any antibody that can recognize and specifically bind to a component involved in TGF-β signaling pathway is useful in the present invention. The invention should not be construed to be limited to any one type of antibody, either known or heretofore unknown, provided that the antibody can specifically bind to a component involved in TGF-β signaling pathway. Methods of making and using such antibodies are well known in the art. For example, the generation of polyclonal antibodies can be accomplished by inoculating the desired animal with the antigen and isolating antibodies which specifically bind the antigen therefrom. Monoclonal antibodies directed against full length or peptide fragments of a protein or peptide may be prepared using any well known monoclonal antibody preparation procedures, such as those described, for example, in Harlow et al. (1989, Antibodies, A Laboratory Manual, Cold Spring Harbor, N.Y.) and in Tuszynski et al. (1988, Blood 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein. However, the invention should not be construed as being limited solely to methods and compositions including these antibodies, but should be construed to include other antibodies, as that term is defined elsewhere herein.

In some instances, it is desirable to prepare monoclonal antibodies from various mammalian hosts, such as rodents (e.g., mice), primates (e.g., humans), etc. Descriptions of techniques for preparing such monoclonal antibodies are well known and are described, for example, in Harlow et al., ANTIBODIES: A LABORATORY MANUAL, COLD SPRING HARBOR LABORATORY, Cold Spring Harbor, N.Y. (1988); Harlow et al., USING ANTIBODIES: A LABORATORY MANUAL, (Cold Spring Harbor Press, New York, 1998); Breitling et al., RECOMBINANT ANTIBODIES (Wiley-Spektrum, 1999); and Kohler et al., 1997

*Nature* 256: 495-497; U.S. Pat. No. 5,693,762; U.S. Pat. No. 5,693,761; U.S. Pat. No. 5,585,089; U.S. Pat. No. 6,180,370.

Nucleic acid encoding an antibody obtained using the procedures described herein may be cloned and sequenced using technology which is available in the art, and is described, for example, in Wright et al. (1992, Critical Rev in Immunol 12:125-168) and the references cited therein. Further, the antibody of the invention may be "humanized" using the technology described in Wright et al. (supra) and in the references cited therein, and in Gu et al, (1997, Thrombosis and Hematocyst 77:755-759).

Alternatively, antibodies can be generated using phage display technology. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase, cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J Mol Biol 222:581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J Mol Biol 248:97-105).

The invention encompasses polyclonal, monoclonal, synthetic antibodies, and the like. One skilled in the art would understand, based upon the disclosure provided herein, that the crucial feature of the antibody of the invention is that the antibody specifically bind with a component involved in TGF-$\beta$ signaling pathway.

ALK5 Inhibitor

In addition to a genetic approach, the invention includes the use of small compounds to inhibit a component of the TGF-$\beta$ signaling pathway. By way of a non-limiting example, activin-like kinase 5 (ALK5, a key TGF-$\beta$ receptor I that pairs with TGF-$\beta$ receptor II for signaling) inhibitors (e.g., SB-505124 and SB-431542) are useful in inhibiting a component of the TGF-$\beta$ signaling pathway in a macrophage thereby enhancing the ability of the macrophage to phagocytosize A$\beta$. The disclosure presented herein demonstrates that activin-like kinase 5 inhibitors were able to inhibit a component of the TGF-$\beta$ signaling pathway and increase macrophage A$\beta$ phagocytosis. Thus, both genetic and pharmacologic means of TGF-$\beta$ signaling inhibition is included in the invention to promote enhanced macrophage A$\beta$ phagocytosis and therefore clearance and resolution of this hallmark pathological peptide in Alzheimer's disease.

Activator of Smad1/5/8

This aspect of the invention is based on the discovery that inhibition of TGF-$\beta$-activated Smad2/3 signaling pathway in peripheral macrophages exhibited hyperactivation of alternative bone morphogenic protein-activated Smad1/5/8 signaling which corresponded to increased macrophage A$\beta$ phagocytosis activity. Thus, the invention also encompasses activating the Smad1/5/8 signaling pathway in peripheral macrophages in order to increase macrophage A$\beta$ phagocytosis activity. In some instances, the invention includes activating the bone morphogenic protein-Smad1/5/8 signaling in peripheral macrophages. In one embodiment, this may involve administering bone morphogenic protein or a bone morphogenic protein-Smad1/5/8 pathway agonist compound directly into the mammal, preferably human, that exhibits symptoms of Alzheimer's disease In other related aspects, the invention includes an isolated nucleic acid encoding an activator of a component of bone morphogenie protein-Smad1/5/8 signaling, wherein the activator can be expressed in a cell using know molecular biology techniques. For example, the desired activator is operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, N.Y.), and in Ausubel et al. (1997, Current Protocols in Molecular Biology, John Wiley & Sons, New York).

The desired polynucleotide corresponding to a desired activator can be cloned into a number of types of vectors. However, the present invention should not be construed to be limited to any particular vector. Instead, the present invention should be construed to encompass a wide plethora of vectors which are readily available and/or well-known in the art. For example, a desired polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

In specific embodiments, the expression vector is selected from the group consisting of a viral vector, a bacterial vector and a mammalian cell vector. Numerous expression vector systems exist that comprise at least a part or all of the compositions discussed above. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al, (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the desired polynucleotide, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment, A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. No. 4,683,202, U.S. Pat. No. 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al, (2001). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

In order to assess the expression of the desired polynucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479: 79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a regulator.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al, (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Any DNA vector or delivery vehicle can be utilized to transfer the desired polynucleotide to a cell in vitro or in vivo. In the case where a non-viral delivery system is utilized, a preferred delivery vehicle is a liposome. The above-mentioned delivery systems and protocols therefore can be found in Gene Targeting Protocols, 2ed., pp 1-35 (2002) and Gene Transfer and Expression Protocols, Vol. 7, Murray ed., pp 81-89 (1991).

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Modified Cell

One skilled in the art would understand that the methods discussed relating to expressing an activator in a cell is equally applicable to expressing an inhibitor into a cell. That is, the instant invention provides a cell-based system for expressing an inhibitor of a component of TGF-β signaling pathway, an activator of a component of bone morphogenic protein-Smad1/5/8 signaling pathway, or any combinations thereof.

The invention includes a cell that has been modified to possess a heightened Aβ phagocytosis and central nervous system penetration capacity as compared to an otherwise identical cell not modified according to the present invention. The modified cell is suitable for administration to a mammalian recipient alone or in combination with other therapies. Thus, the invention also includes a cell with heighted Aβ phagocytosis and central nervous system penetration capacity or otherwise referred to as a "sensitized" cell. The sensitized cell leads to en masse brain infiltration and beneficial cerebral Aβ clearance by the cell.

Therapeutic Application

The present invention includes an inhibitor of a component of TGF-β, an activator of morphogenic protein-Smad1/5/8 signaling pathway, or any combinations thereof. The invention also includes a cell having heighted Aβ phagocytosis and increased central nervous system penetration capability as compared to an otherwise identical cell not modified according to the present invention.

Ex vivo procedures are well known in the art and are discussed more fully below. Briefly, cells are isolated from a mammal (preferably a human) and modified to enhance its Aβ phagoeytosis activity according to the methods of the invention. For example, the cell is modified to have a component of TGF-β inhibited, a component of morphogenic protein-Smad1/5/8 signaling pathway activated, or any combinations thereof. The heighted Aβ phagocytic cell can be administered to a mammalian recipient to provide a therapeutic benefit. The mammalian recipient may be a human and the cell so modified can be autologous with respect to the recipient. Alternatively, the cells can be allogeneic, syngeneic or xenogeneic with respect to the recipient.

The procedure for ex vivo expansion is described in U.S. Pat. No. 5,199,942, incorporated herein by reference, can be applied to the cells of the present invention. Other suitable methods are known in the art, therefore the present invention is not limited to any particular method of ex vivo expansion of the cells.

In addition to using a cell-based therapy in terms of ex vivo therapy, the present invention also provides compositions and methods for in vivo therapy to enhance Aβ phagocytosis activity of endogenous peripheral macrophages. With respect to in vivo therapy, the present invention provides a use of an inhibitor of a component of the TGF-β pathway, an activator of morphogenic protein-Smad1/5/8 signaling pathway, or any combinations thereof as a means to enhance Aβ phagocytosis activity of peripheral macrophages and enhance cerebral Aβ clearance by the macrophage. As such, the cell-based therapy used for in vivo immunization comprises an inhibitor component, an activator component, or any combination thereof, wherein the cell-based therapy is able to enhance central nervous system penetration and/or Aβ phagocytosis activity of endogenous peripheral macrophages.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a nanoparticle including but not limited to a liposome, an aggregated protein or a transporter molecule.

Cells containing the desired nucleic acid may also contain a suicide gene i.e., a gene which encodes a product that can be used to destroy the cell. In many gene therapy situations, it is desirable to be able to express a gene for therapeutic purposes in a host, cell but also to have the capacity to destroy the host cell at will. The nucleic acid sequence corresponding to the inhibitor and/or activator of the invention can be linked to a suicide gene, whose expression is not activated in the absence of a suicide gene activator compound. When death of the cell in which both the inhibitor/activator and the suicide gene have been introduced is desired, the suicide gene activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidylate kinase (Tdk::Tmk) and AZT; and deoxycytidine kinase and cytosine arabinoside.

In another embodiment, the compounds of the present invention may be used in combination with existing therapeutic agents used to treat Alzheimer's disease. In some instances, the compounds of the invention may be used in combination with these therapeutic agents to enhance the anti-amyloid therapeutic effect of the therapeutic agent.

In order to evaluate potential therapeutic efficacy of the compounds of the invention in combination with the anti-amyloid therapeutics described elsewhere herein, these combinations may be tested for anti-amyloid therapeutic activity according to methods known in the art.

In some embodiments, an effective amount of a compound of the invention and an anti-amyloid therapeutic agent is a synergistic amount. As used herein, a "synergistic combination" or a "synergistic amount" of a compound of the invention and a therapeutic agent is a combination or amount that is more effective in the therapeutic or prophylactic treatment of a disease than the incremental improvement in treatment outcome that could be predicted or expected from a merely additive combination of (i) the therapeutic or prophylactic benefit of the compound of the invention when administered at that same dosage as a monotherapy and (ii) the therapeutic or prophylactic benefit of the therapeutic agent when administered at the same dosage as a monotherapy.

Dosage and Formulation (Pharmaceutical Compositions)

The present invention envisions treating a disease, for example, Alzheimer's disease and the likes, in a mammal by the administration of a composition of the invention, e.g. an inhibitor of a component of TGF-β signaling pathway, an activator of bone morphogenic protein-Smad1/5/8 signaling pathway, or any combination thereof.

Administration of the composition in accordance with the present invention may be continuous or intermittent, depending, for example, upon the recipient's physiological condition, whether the purpose of the administration is therapeutic or prophylactic, and other factors known to skilled practitioners. The administration of the compositions of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art One or more suitable unit dosage forms having the compositions of the invention, which, as discussed elsewhere herein, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes, as well as by direct injection into the diseased tissue. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the compositions of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The expression vectors, transduced cells, polynucleotides and polypeptides (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Alzheimer's disease is the most common dementia and is pathologically characterized by deposition of amyloid-$\beta$ peptide (A$\beta$) into $\beta$-amyloid plaques, neuronal injury and low-level, chronic activation of brain inflammation and immunity (Selkoe, 2001, Physiol Rev. 81 (2):741-66). Transforming growth factor-$\beta$s (TGF-$\beta$s) are pleiotropic cytokines that have key roles in immune cell activation, inflammation and repair after injury (Li et al., 2006, Annu Rev Immunol. 24:99-146).

The results presented herein relate to genetically interrupting TGF-$\beta$ and downstream Smad2/3 signaling (TGF-$\beta$-Smad2/3) in innate immune cells by inducing expression of CD11c promoter-driven dominant-negative TGF-$\beta$ receptor type II in C57BL/6 mice (CD11c-DNR) (Laouar et al., 2005, Nat Immunol. 6 (6):600-7), crossing these mice with mice overexpressing mutant human amyloid precursor protein, the Tg2576 Alzheimer's disease mouse model (Hsiao, et al. 1996, Science 274 (5284):99-102), and evaluating Alzheimer's disease-like pathology.

Aged double-transgenic mice showed complete mitigation of Tg2576-associated hyperactivity and partial mitigation of defective spatial working memory. Brain parenchymal and cerebrovascular $\beta$-amyloid deposits and A$\beta$ abundance were markedly (up to 90%) attenuated in Tg2576-CD11c-DNR mice. This was associated with increased infiltration of A$\beta$-containing peripheral macrophages around cerebral vessels and $\beta$-amyloid plaques. In vitro, cultures of peripheral macrophages, but not microglia, from CD11c-DNR mice showed blockade of classical TGF-$\beta$-activated Smad2/3 but also showed hyperactivation of alternative bone morphogenic protein-activated Smad1/5/8 signaling and increased A$\beta$ phagocytosis. Similar effects were noted after pharmacological inhibition of activin-like kinase-5, a type I TGF-$\beta$ receptor. Taken together, the results presented herein suggest that blockade of TGF-$\beta$-Smad2/3 signaling in peripheral macrophages represents a therapeutic target for Alzheimer's disease.

The materials and methods employed in the experiments disclosed herein are now described.

Mice

Tg2576 mice were obtained from Taconic and maintained as heterozygotes on a hybrid C57BL/6×SJL background by intercrossing breeding pairs (Hsiao, et al. 1996, Science 274 (5284):99-102). CD11c-DNR mice (Laouar et al., 2005, Nat Immunol. 6 (6):600-7) were maintained as heterozygotes on a C57BL/6 background and crossed them with Tg2576 mice to yield four genotypes of littermates. Mice between 16 and 18 months of age were studied: wild-type (n=14, four males and ten females), CD11c-DNR (6 males), Tg2576 (n=12, five males and 7 females) and Tg2576-CD11c-DNR (n=10, seven males and three females). A younger (12-month-old) cohort of these mice were also studied (during initial deposition of β-amyloid (Hsiao, et al. 1996, Science 274 (5284):99-102)), including Tg2576 (n=5, three females and two males) and Tg2576-CD11c-DNR (n=5, three females and two males) genotypes. An accelerated doubly-transgenic mouse model of Alzheimer's disease (Tg(APPswe,PSEN1dE9)85 was obtained (Jankowsky et al., 2001, Biomol. Eng 17:157-165), designated Tg(APP,PSEN) herein) from the Jackson Laboratory, and these mice were maintained as heterozygotes on a hybrid C57BL/6×C3H background by intercrossing breeding pairs. CD11c-DNR mice were also bred to Tg(APP,PSEN) mice, and both Tg(APP,PSEN) mice (n=5, three males and two females) and Tg(APP,PSEN)-CD11c-DNR mice (n=5, three males and two females) were analyzed at 15 months of age. All mice were housed in a 12-hr light and dark cycle at Yale University in The Anylan Center Animal Housing Facility, and the Yale University Institutional Animal Care and Use Committee approved all experiments, which was conducted in accordance with Yale Animal Resources Center guidelines.

Tissue Handling

Mice were sacrificed with isofluorane and transcarclially perfused them with ice-cold PBS. Brains were rapidly isolated and quartered as previously described (Tan et al., 2002, Nat. Neurosci. 5:1288) using a mouse brain slicer (World Precision Instruments). Anterior quarters were weighed and then snap-froze and randomly assigned one of these to electric homogenization (Tekmar Tissuemizer) in cell lysis buffer (containing 20 mM Tris pH 7.5, 150 mM NaCl, 1 mM EDTA, 1 mM EGTA, 1% vol/vol Triton X-100, 2.5 mM sodium pyrophosphate, 1 mM β-glycerolphosphate, 1 mM Na3VO4 1 µg/ml leupeptin and 1 mM PMSF) for protein isolation. Protein homogenates were centrifuged at 13,000 g for 30 min at 4° C., removed the supernatant (detergent-soluble fraction), treated the remaining pellet with 5 M guanidine HCl and solubilized it by occasional mixing on ice for 30 min (guanidine HCl-soluble fraction). Posterior quarters were immersion-fixed in 4% (vol/vol) paraformaldehyde for 48 h at 4° C., randomly assigned one posterior quarter for cryoprotection in a graded series of sucrose diluted in PBS (10% to 20% to 30%, each incubation step at 4° C. overnight) and embedded cerebral pieces in optimal cutting temperature compound (OCT, Tissue-Tek, Sakura) for cryosectioning.

Immunohistochemistry and Morphometry

For immunohistochemistry (Aβ, GFAP and CD45 staining) and thioflavin S histochemistry, four 10-µm coronal brain sections per mouse were cryosectioned (spaced 50 µm apart) using a Leica model CM1850 freezing microtome (Leica), applied brain sections to Superfrost Plus Gold slides (Fisher Scientific) and allowed slides to air-dry for 5 min at 25° C. Immunohistochemical staining was performed with the VectaStain Elite ABC kit (Vector Laboratories) in accordance with the manufacturer's instructions with 3'-3' diaminobenzadine as a chromogen (Sigma-Aldrich). Histochemistry was performed with thioflavin S (a fluorescent dye that binds to the β-pleated sheet conformation present in mature β-amyloid plaques) by diluting 1% (w/vol) of practical-grade thioflavin S (Sigma-Aldrich) in 70% vol/vol ethanol. The solution was filtered and then used to incubate the slides for 10 min at 25° C. followed by three rinses for 5 min each in 70% ethanol and a final rinse in PBS. The slides were then air-dried in the dark, mounted in fluorescent mounting media containing DAPI (Prolong Gold; Invitrogen—Molecular Probes) and viewed with an automated Olympus BX-61 microscope equipped for bright and dark fields. For confocal microscopy analyses, 25-µm coronal brain sections were cryosectioned (spaced 50 µm apart), applied PAP-pen (Invitrogen) and preblocked in serum-free protein block (Dako) for 30 min at 25° C. Primary antibody was then diluted in serum-free protein block and the slides were incubated overnight at 4° C. After three rinses for 5 min each in PBS, the slides were incubated for 1 h at 25° C. with appropriate Alexa Fluor 488-, Alexa Fluor 594- or Alexa Fluor 647-conjugated secondary antibodies (Invitrogen-Molecular Probes). After an additional three rinses for 5 min each with PBS at 25° C., the slides were air-dried in the dark and finally mounted with Prolong Gold containing DAPI (Invitrogen-Molecular Probes). Fluorophores were imaged in separate channels with a Zeiss 510 META laser-scanning confocal microscope (Carl Zeiss Microimaging) and projections were generated from three-dimensional-rendered optical sections, Various antibodies were used to the following proteins for immunohistochemistry: cow GFAP (1:1,000; Dako), human Aβ (clone 4G8, 1:250; Covance Research Products), mouse CD45 or CD11b (1:200; Serotec), mouse CD11c (1:50; Thermo Fisher Scientific-Pierce Biotechnology) and mouse Ly-6C (conjugated with biotin, 1:100; BD Biosciences-Pharmingen).

Image Analysis

Images of brain sections stained with antibodies to 408, GFAP or CD45 or with thioflavin S were acquired using an automated Olympus BX-61 microscope with an attached Magnafire CCD camera system and Scion Image for Windows software, release alpha 4.0.3.2 (Scion) as previously described (Tan et al., 2002, Nat. Neurosci 5:1288-1293). Images of four 10-µm sections through each anatomic region of interest were captured, and a threshold optical density that best discriminated staining from background was obtained. For β-amyloid, GFAP, CD45 and thioflavin S burden analyses, data are reported as the percentage of labeled area captured (positive pixels) divided by the full area captured (total pixels). CAA scores according to previous methods (Wyss-Coray, et al., 2001, Nat Med. 7 (5):612-18) were determined. For β-amyloid plaque (408 or thioflavin S staining) morphometric analyses (Tan et al., 2002, Nat. Neurosci 5:1288-), maximum diameters of plaques (small, <25 µm; medium, 25-50 µm; or large, >50 µm) were calculated by quantitative image analyses, and an examiner blind to sample identities totaled numbers of plaques falling into each diameter category. For semiquantitative immunofluorescence analysis of CD45+CD11b+ macrophages in individual progeny from Tg (APP,PSEN)-CD11c-DNR matings, four brain sections per mouse were blindly scored using a five-point semiquantitative scale.

Statistical Analyses

In instances of single comparisons of the means, Levene's test was used for equality of the variance followed by t-test for independent samples to assess significance, except for semiquantitative histology (that is, 'CAA Score' and 'CD45+CD11b+ infiltrating macrophages' data), where the Mann-Whitney U-test was used. In instances of multiple means comparisons, ANOVA was used, followed by post hoc comparison by Fisher's LSD (for behavioral data) or Bonferroni's method (for all other analyses). For all analyses, alpha levels was set at 0.05 (SPSS for Windows, release 15.0, SPSS Inc.). An examiner blinded to sample identities performed all analyses, and the code was not broken until analyses were completed.

Behavioral Analyses

Exploratory activity was evaluated by individually placing mice into a novel environment with fresh bedding, and monitoring their activity for 20 min by an overhead CCD camera and computerized tracking system (Ethovision®; Noldus). Data are reported as distance traveled (cm) per 2.5-min time bin. Spontaneous alternation and total arm entries were assayed essentially as described elsewhere (Hsiao et al., 1996 Science 274: 99-102; Holcomb et al., 1998 Nat. Med. 4: 97-100; Holcomb et al., 1999 Behav. Genet. 29: 177-185). Briefly, mice were individually placed in one arm of a radially symmetric Y-maze made of opaque black acrylic (arms: 40 cm long, 4 cm wide; walls: 30 cm tall), the sequence of arm entries and total number of entries was recorded over a period of 8 min, beginning when the animal first entered the central area. Percentage of alternation was defined as the number of sequential triplets of arm visits during the session as a proportion of total triplets of arm visits (i.e., visiting arms A-B-C or C-B-A constituted a sequential triplet, while A-B-A or A-C-A did not).

Testing in the Morris water maze was performed essentially as previously described (Hsiao et al., 1996 Science 274: 99-102; Pittenger et al., 2002 Neuron 34: 447-462). The water maze consisted of a circular pool (diameter of 1 m) filled with water made opaque with non-toxic white paint maintained at 23-26° C. The 12.5 cm square plexiglass platform was located 1 cm below the water surface. After a minimum of 20 min habituation to the room, mice were placed in the pool and they were allowed to search for the platform for 60 s. Animals were guided to the platform that did not locate it within 60 s, and allowed to remain there for 15 s before returning them to their cages. Mice were trained four times per day with a 20 min inter-trial interval. On the first two days, a visible cue was placed on the platform and randomly varied its location among four possible locations. Then, the animals were trained for an additional 10 days with the platform invisible below the surface of the water and in an invariant location (counterbalanced across mice). Probe trials were performed, in which the animal was placed in the pool in the absence of the escape platform and its search was monitored for 30 s, on days 5 and 10 of hidden platform training. All behavioral tests were performed in a room (6'×8') with indirect lighting and multiple visible cues on the walls. Trials were recorded using an overhead CCD camera and analyzed using Noldus:Ethovision®. All trials were performed at the same time of day (±1 h), during the animals' light phase. An examiner who was blind to mouse genotype performed behavioral analyses.

Aβ ELISA and Bio-Plex Cytokine Assays

Brain homogenates (detergent- or 5 M guanidine HCl-soluble protein fractions 5) or EDTA-treated plasma samples from Tg2576 or Tg2576/CD11c-DNR mice at 17-18 months of age (taken at time of sacrifice) were analyzed by sandwich ELISA for human $A\beta_{1-40}$ or $A\beta_{1-42}$, or total human $A\beta$ (estimated by summing $A\beta_{1-40}$ and $A\beta_{1-42}$ values) using commercially available kits strictly according to the manufacturer's instruction (Invitrogen-Biosource). Dilution factors of 1:10, 1:5,000, and 1:4 for detergent-soluble brain homogenates, guanidine HCl-soluble brain homogenates, and plasma samples, respectively, were used, and all samples fell within the linear range of standard curves. ELISA values are reported as ng of $A\beta_{1-x}$/wet g (or mg) of brain. Cytokines in detergent-soluble brain homogenates were assayed at a 1:1 dilution using the Beadlyte® mouse multi-eytokine detection system 2 [allows simultaneous detection of interleukin (Il)-1β, Il-2, Il-4, Il-5, Il-6, Il-10, Il-12(p70), tumor necrosis factor-α, interferon-γ, and granulocyte-macrophage colony stimulating factor; Millipore] in conjunction with the Bio-Plex™ multiplex cytokine bead reader (Bio-Rad Laboratories) according to the manufacturer's instruction.

Fluorescent-Activated Cell Sorter (FACS) Analysis

FACS analysis was performed on brain mononuclear cells of hematopoetic origin according to previously published methods with minor modifications (Juedes, A. E. & Ruddle, 2001 J. Immunol. 166: 5168-5175). Briefly, brains from Tg(APP,PSEN) and Tg(APP,PSEN)/CD11c-DNR mice under deep isofluorane anesthesia (n=5 per group; 3 males, 2 females 15 months of age) were rapidly isolated and quartered as described elsewhere herein. Cerebral quarters were placed on ice in RPMI 1640 media (Invitrogen-Gibco), and homogenized in an Eppendorf hand homogenizer (eight strokes) to obtain single cell suspensions. Samples of the same genotype were pooled and mononuclear cells were isolated by discontinuous Percoll gradient (GE Healthcare-Pharmacia). These cells were rinsed in FACS buffer (1% FCS, 0.1% w/v sodium azide), incubated with Fc Block™ (BD Biosciences-Pharmingen) for 20 min on ice, and stained with FITC-conjugated CD45 (1:100), APC-conjugated CD11b (1:200), and PE-conjugated CD11c (1:50) antibodies for 20 min on ice (all FACS antibodies were from BD Biosciences-Phanningen). The cells were then rinsed three times in FACS buffer, and analyzed using a FACSCaliber™ instrument (BD Biosciences). As previously described in Juedes, A. E. & Ruddle, mononuclear cells that were CD11b positive and intermediate CD45 expressers (CD11b+CD45int) were taken as resident microglia whereas CD11b+CD45high cells were taken as infiltrating peripheral macrophages (MΦ).

Cell Isolation and Culture

Cortical microglia were isolated from neonatal (1-2 day-old) CD11c-DNR or wild-type C57BL/6 mice according to previously published methods (Tan et al., 1999 Science 286: 2352-2355; Town et al., 2006 J. Immunol, 176: 3804-3812), Briefly, brains were isolated under sterile conditions and cerebral cortices were incubated in tripsin-EDTA (Invitrogen-Gibco) for 15 min at 37° C. Complete RPMI 1640 medium (supplemented with 10% FCS and 1 mM penicillin-streptomycin) was then added and brains were dissociated by trituration. Subsequently, cerebral cortex material was plated in 25 cm² flasks (Fisher Scientific), and the media was changed every 2-3 days. When the appearance of microglia was noted (typically 14 days after plating), culture media was exchanged with RPMI 1640 medium supplemented with 5% FCS, and the microglia were isolated by shaking in an incubator-shaker at 200 rpm for 2 h at 37° C. Peripheral MΦ were isolated from adult CD11c-DNR or wild-type C57BL/6 mice according to standard immunological methods by intraperitoneally (i.p.) injecting mice with 900 μL of 3% (w/v) sterile thioglycollate solution diluted in PBS. Four days later, mice were injected i.p. with 10 mL of ice-cold PBS for peritoneal lavage. Peripheral MΦ were then plated with complete medium (DMEM supplemented with 10% FCS and 1 mM penicillin streptomycin) and allowed to rest overnight. The following morning, MΦ were rinsed four times in ambient temperature PBS and fresh medium was added, Cultures of microglia and peripheral MΦ were both >95% pure as determined by immunofluorescent staining with CD11b and CD45 antibodies.

Aβ Phagocytosis Assay

Peripheral MΦ from CD11c-DNR or wild-type C57BL/6 mice were plated on glass coverslips in 24-well culture plates (Fisher Scientific) at 5×10⁵ cells/well in complete DMEM as described elsewhere herein. Human synthetic Aβ$_{1-42}$ conjugated with Hilyte Fluor™ 488 (Aβ$_{488}$; AnaSpec) was resuspended in dH$_2$O at 1 mg/mL and pre-aggregated for 24 h at 37° C. Aβ$_{488}$ was added at 1 µg/mL to MΦ cultures and cells were pulsed for 4 h at 37° C. MΦ were then rinsed three times in ambient-temperature PBS, and chased for 15 min to allow Aβ$_{488}$ to concentrate into phagolysosomes. After an additional two rinses in complete DMEM and then two final rinses in PBS, coverslips were mounted in ProLong Gold™ fluorescent mounting medium containing DAPI for confocal microscopy. Three random 10× magnification fields were acquired and the data were reported two ways: as Aβ$_{488}$ labeled area (similar to "burden" analysis) or number of MΦ/field containing Aβ$_{488}$. In parallel experiments, peripheral MΦ from CD11c-DNR or wild-type mice were plated at 1.5×10$^6$ cells/well in 6-well culture plates (Fisher Scientific) in complete DMEM. Human synthetic Aβ$_{1-42}$ (unlabeled; Invitrogen-Biosource) was resuspended and pre-aggregated as described elsewhere herein, and MΦ were cultured as mentioned elsewhere herein, except that the cells were lysed in cell lysis buffer and subjected to Western blot for Aβ as described elsewhere herein.

Western Immunoblot

Microglia or peripheral MΦ from wild-type or CD11c-DNR mice were plated at 1×10$^6$ cells/well in 6-well tissue culture plates (BD Biosciences-Falcon) containing complete RPMI 1640 media or complete DMEM, respectively. These cells were then treated with a dose-range of recombinant TGF-β1 (R&D Systems; 1, 5, or 10 ng/mL) in the presence or absence of lipopolysachharide (LPS, 50 ng/mL) for 30 min. In a separate set of experiments, these cells were pre-treated for 1 h with ALK5 inhibitors SB-505124 or SB-431542 (Sigma-Aldrich; used at 0.1, 1.0, or 10.0 µM) and 5 ng/mL of recombinant TGF-β1 was added. For Aβ phagocytosis assay, MΦ were pulse-chased with Aβ as described elsewhere herein. Cells were rinsed in ice-cold PBS three times, and lysed ice-cold lysis buffer (containing 20 mM Tris-HCl pH 7.5, 150 mM NaCl, 1 mM Na$_2$EDTA, 1 mM EGTA, 1% v/v Triton X-100, 2.5 mM sodium pyrophosphate, 1 mM glycerophosphate, 1 mM Na$_3$VO$_4$, 1 µg/ml leupeptin, and 1 mM PMSF). After lysis for 30 min on ice, cell lysates were centrifuged at 15,000×g for 30 min, and supernatants were aliquoted for Western blot analysis. Protein concentration was determined using the Bradford method, and aliquots corresponding to 50 µg of protein were run out on 12% Nu-PAGE™ polyacrylamide gels (Invitrogen) and proteins were transferred electrophoretically to Immobilon-P polyvinylidene difluoride membranes (Millipore). Membranes were blocked in blocking buffer (5% w/v nonfat dry milk in Tris-buffered saline containing 1% v/v Tween-20) for 3 h at ambient temperature and incubated overnight at 4° C. with primary polyclonal antibodies directed against total or phosphorylated SMAD2/3, SMAD1/5/8, PAK2, or ERK1/2 (Cell Signaling Technology). Membranes were then rinsed three times for 5 min each in dH2O, and incubated with anti-rabbit secondary antibody conjugated with horseradish peroxidase (diluted at 1/2000 in blocking buffer; GE Healthcare-Amersham Biosciences). After an additional three rinses for 5 min each in dH2O, the membranes were incubated for 5 min at ambient temperature with the enhanced chemiluminescence substrate (Thermo Fisher Scientific-Pierce Biotechnology), exposed to film, and developed.

Detergent-soluble brain homogenates from Tg2576/CD11c-DNR vs. littermate Tg2576 mice were also Western blotted using the same protocol as described elsewhere herein, except that the following primary antibodies were used: monoclonal antibody (mAb) 22C11 against the amino-terminus of APP (Chemicon; 1/2,000, recognizes mouse and human transgene-derived APP), mAb 6E10 against the amino-terminus of human Aβ (Covanee; 1/500, which reveals transgene-derived APP only), or polyclonal (p) antibody against γ-actin (Santa Cruz Biotechnology; 1/200, for a loading control)

Q-PCR

RNA from anterior cerebral pieces was extracted using the TRIzol reagent (invitrogen). Complementary DNA was synthesized using Superscript III reverse transcriptase (Invitrogen). A Taqman™ strategy was used to specifically amplify Tnfa or Il10 from brain cDNA prepared from aged progeny from Tg2576×CD11c-DNR matings using previously described probes and primers (Wang et al., 2004 Nat. Med. 10: 1366-1373). Probes contained a 5' reporter, FAM, and a 3' quencher, BHQ (Biosearch Technologies). The assay was performed on an ABI 7500Fast instrument (Applied Biosystems), and thermal cycling consisted of 95° C. for 4 min and 45 cycles of 95° C. for 30 s and 60° C. for 1 min. To normalize the samples, the same amount of input cDNA in an Hprt1 Q-PCR was used. The ratio of the amount of amplified target gene compared with the amount of Hprt1 cDNA represented the relative levels in each sample.

The results of the experiments disclosed herein are now described.

Example 1

Blocking TGF-β-Smad2/3 Innate Immune Signaling Mitigates Alzheimer-Like Pathology The following experiments were designed to test the hypothesis that blocking innate immune TGF-β signaling would impair cerebral Aβ clearance. However, as detailed below, the results support for the converse hypothesis.

Figure 1:
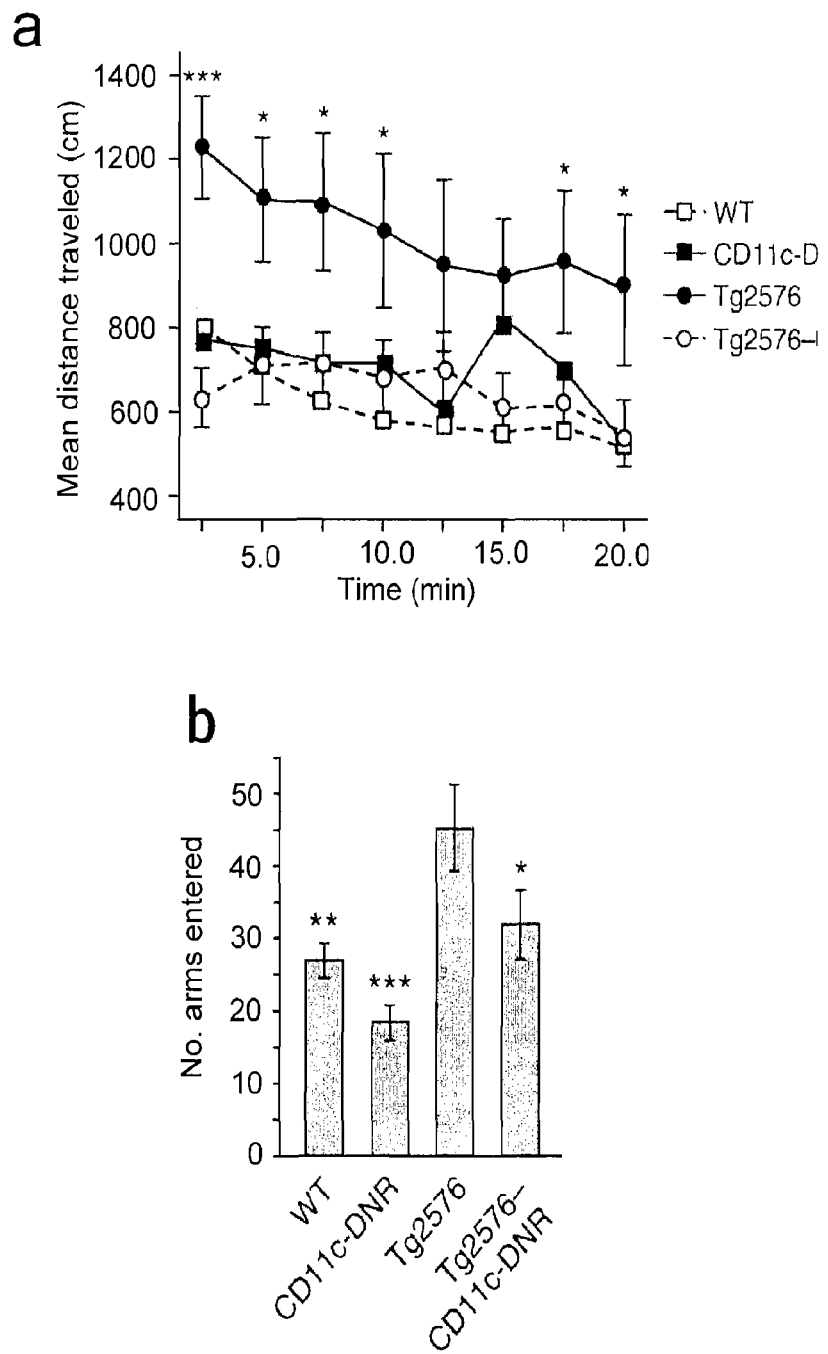
FIG. 1, comprising
Figure 1:
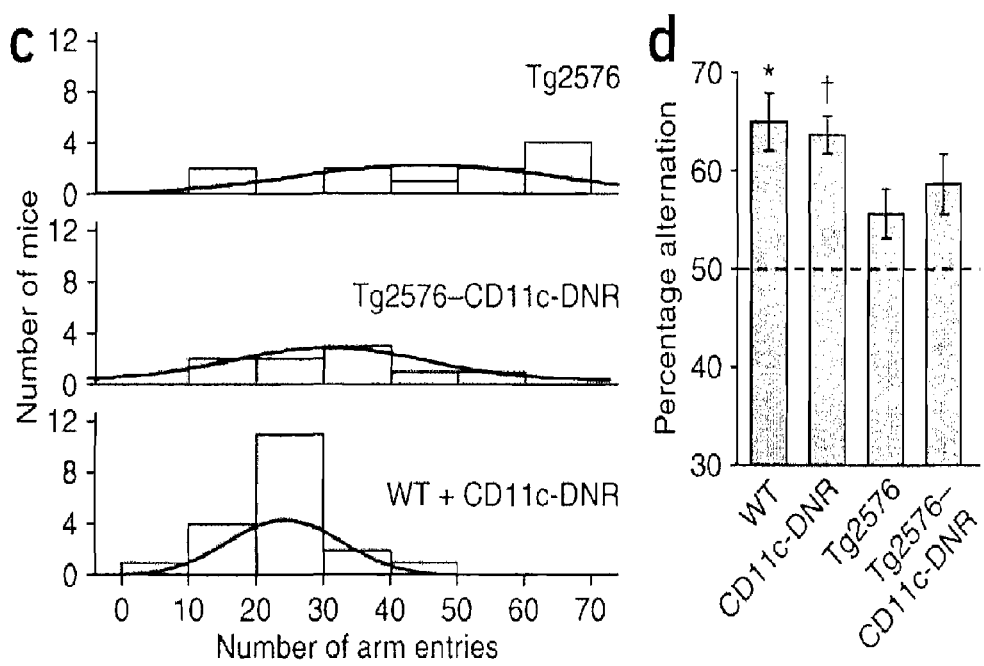

CD11c-DNR transgenic mice (Laouar et al., 2005, Nat Immunol. 6 (6):600-7) were bred to Tg2576 Alzheimer's disease model mice (Hsiao, et al. 1996, Science 274 (5284); 99-102) and behavior of 16-17-month-old progeny was characterized. Tg2576 mice showed hyperactivity (Hsiao, et al. 1996, Science 274 (5284):99-102), probably resulting from disinhibition associated with hippocampal or cortical injury, whereas the Tg2576-CD11c-DNR mice showed complete hyperactivity mitigation (FIG. 1A). Overall analysis of variance (ANOVA) showed significant effects of time (P<0.001) and genotype (P<0.05), and post-hoc comparison showed significant differences when comparing Tg2576 mice to the other groups (FIG. 1A). Similar results were observed during novel Y-maze exploration (Hsiao, et al. 1996, Science 274 (5284):99-102, Holcomb et al., 1998, Nat Med, 4 (1):97-100) (significant effect of genotype, P<0.01; FIG. 1B, 1C). Spontaneous Y-maze alternation, a measure of spatial working memory, was less frequent in Tg2576 versus wild-type (Hsiao, et al, 1996, Science 274 (5284):99-102) or CD11c-DNR control mice, and Tg2576-CD11c-DNR mice had partial amelioration (significant effect trend of genotype, P=0.07; FIG. 1D). ANOVA models revealed that gender did not confound these results (FIG. 10).

Figure 2:
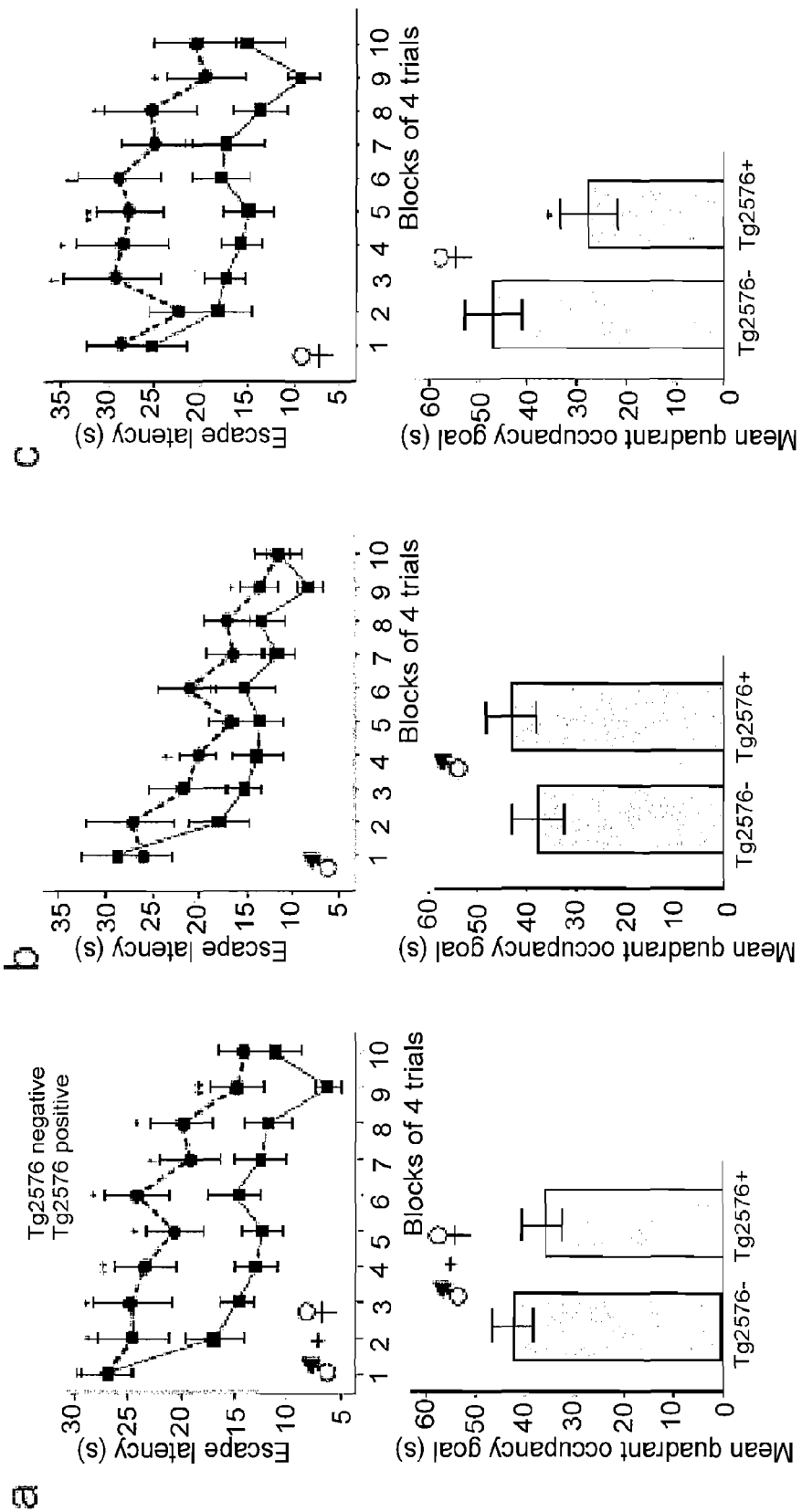
FIG. 2, comprising
Figure 2:
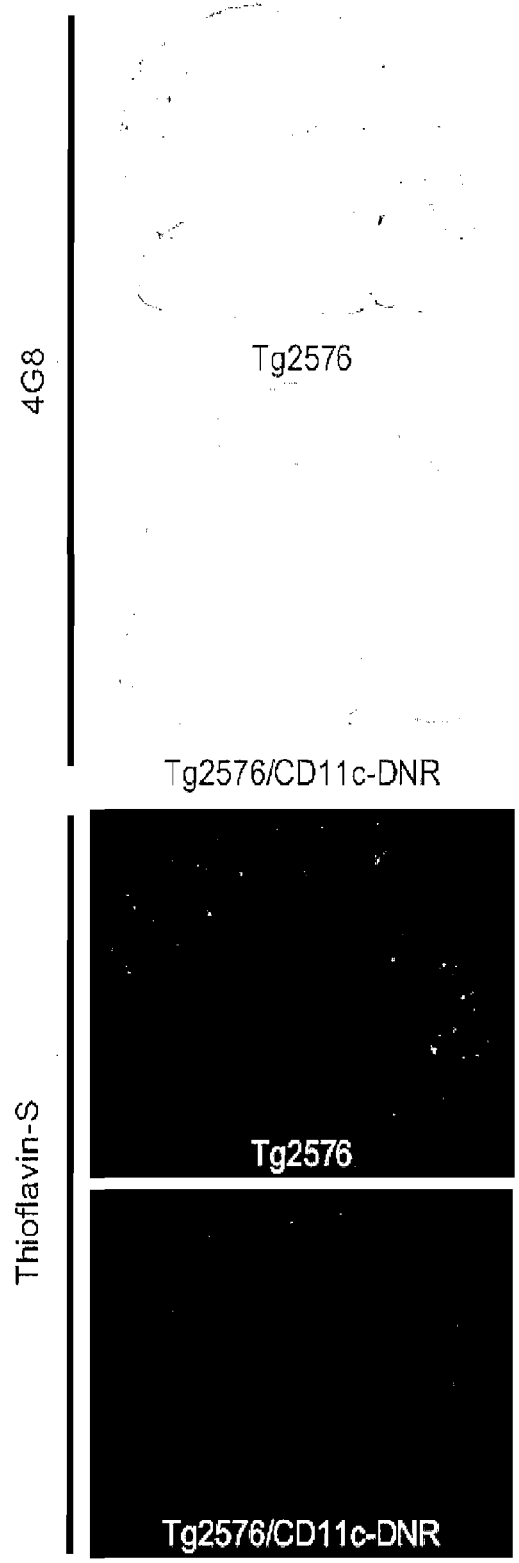
Figure 2:
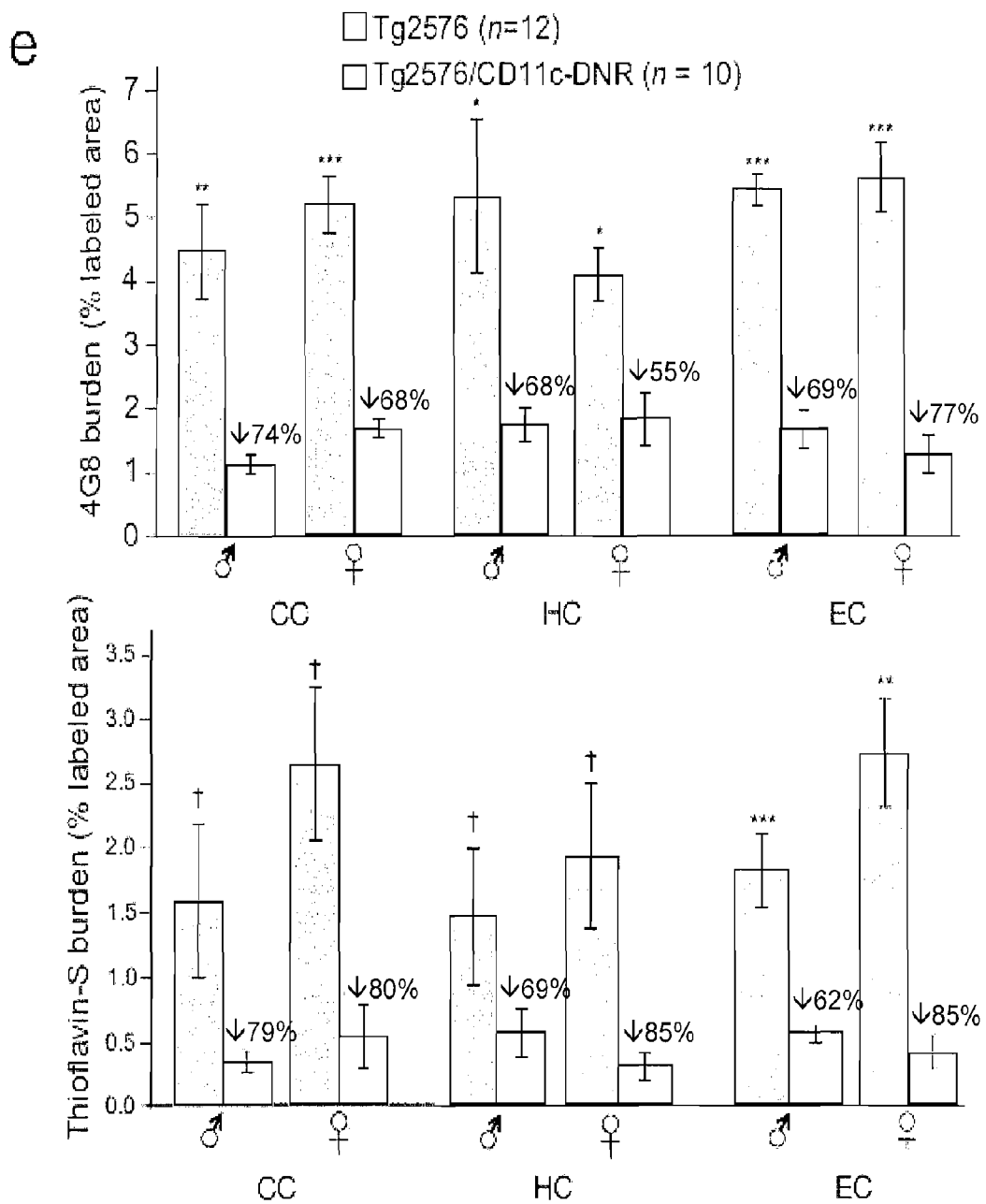

The mice were also tested for spatial reference learning and memory in the Morris water maze. Tg2576 and Tg2576-CD11c-DNR mice did not differ significantly, either during visible platform (learning phase) or hidden platform (probe trials) testing, irrespective of gender (P>0.05, data not shown). However, all mice with the Tg2576 transgene showed greater learning latencies versus Tg2576 transgene-negative mice, but no difference on the day 10 probe trial, whereas female Tg2576-positive mice showed consistent learning and memory deficits in both the learning phase and the probe trial versus female Tg2576-negative mice (FIG. 2A-2C). A similar result has been reported showing that females drive the Tg2576 transgene spatial reference learning and memory deficit (King et al., 1999, Behav Brain Res. 103 (2):145-62). Thus, although the CD11c-DNR transgene completely abrogates Tg2576-associated hyperactivity, it only modestly attenuates defective spatial working memory and does not modify defective spatial reference learning and memory.

The next set of experiments were designed to evaluate Aβ and β-amyloid pathology in 17-18-month-old Tg2576 mice and Tg2576-CD11c-DNR mice using four strategies. Tg2576 mice had typical β-amyloid burden (Irizarry et al., 1997, J Neuropathol Exp Neurol. 56 (9):965-73), which was markedly reduced in cortical areas (entorhinal cortex and cingulate cortex) and the hippocampus by 62-82% in Tg2576-CD11c-DNR mice (FIG. 3A, 3B; FIG. 2D); these effects were gender independent (FIG. 2E) (Callahan et al., 2001, Am J Pathol. 158 (3):1173-7). Morphometric analysis revealed no consistent reductions in the number of small β-amyloid plaques, whereas medium- and large-sized plaque number was substantially reduced by 46-92% in Tg2576 versus Tg2576-CD11c-DNR mice (FIG. 4A-4C), suggesting CD11c-DNR transgene-dependent reduction of β-amyloid plaque maturation.

Figure 3:
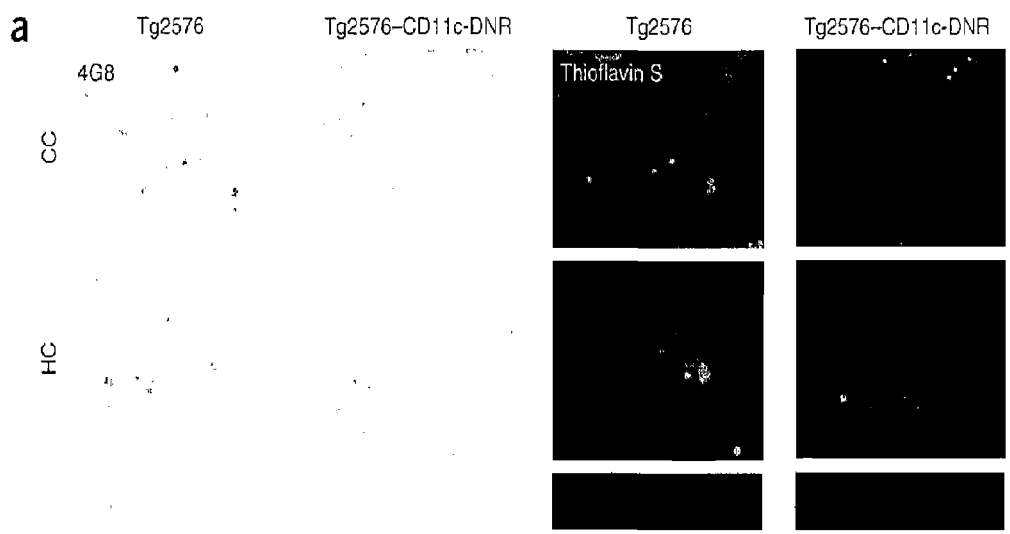
FIG. 3, comprising
Figure 3:
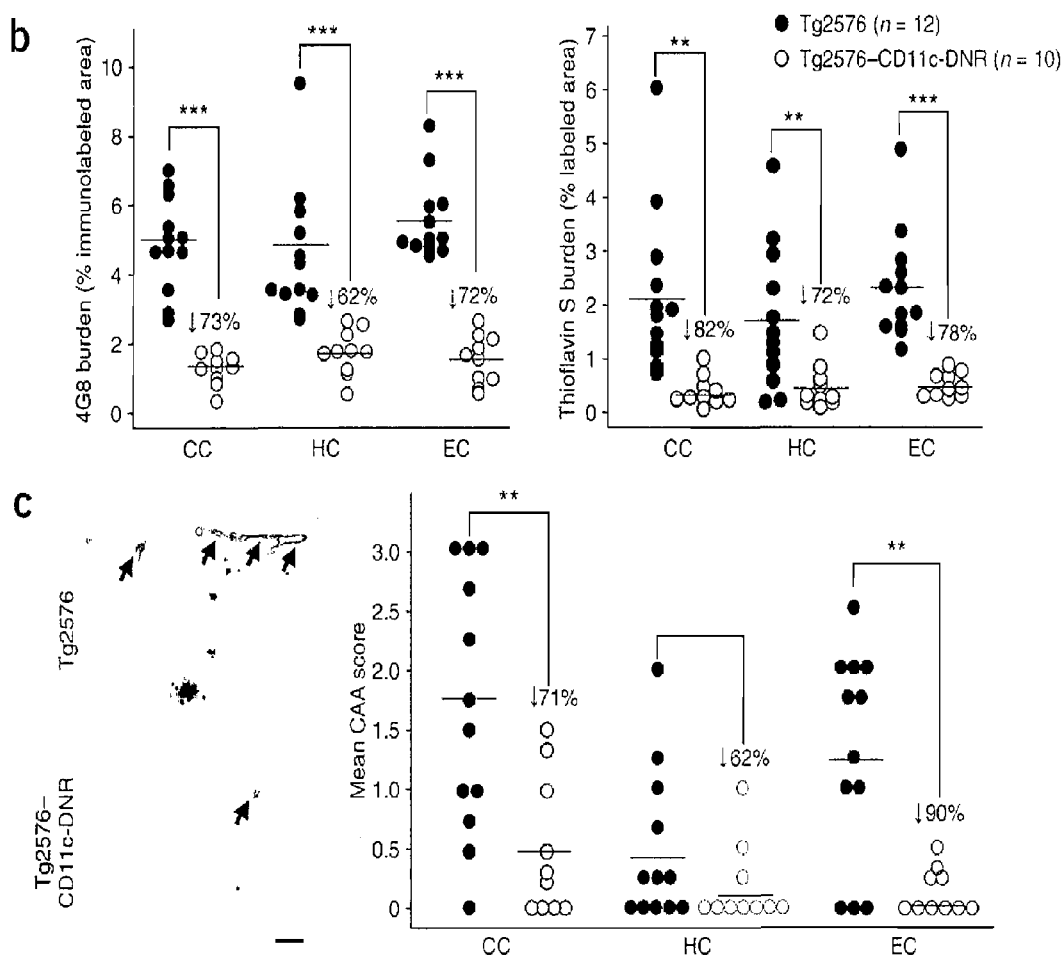
Figure 4:
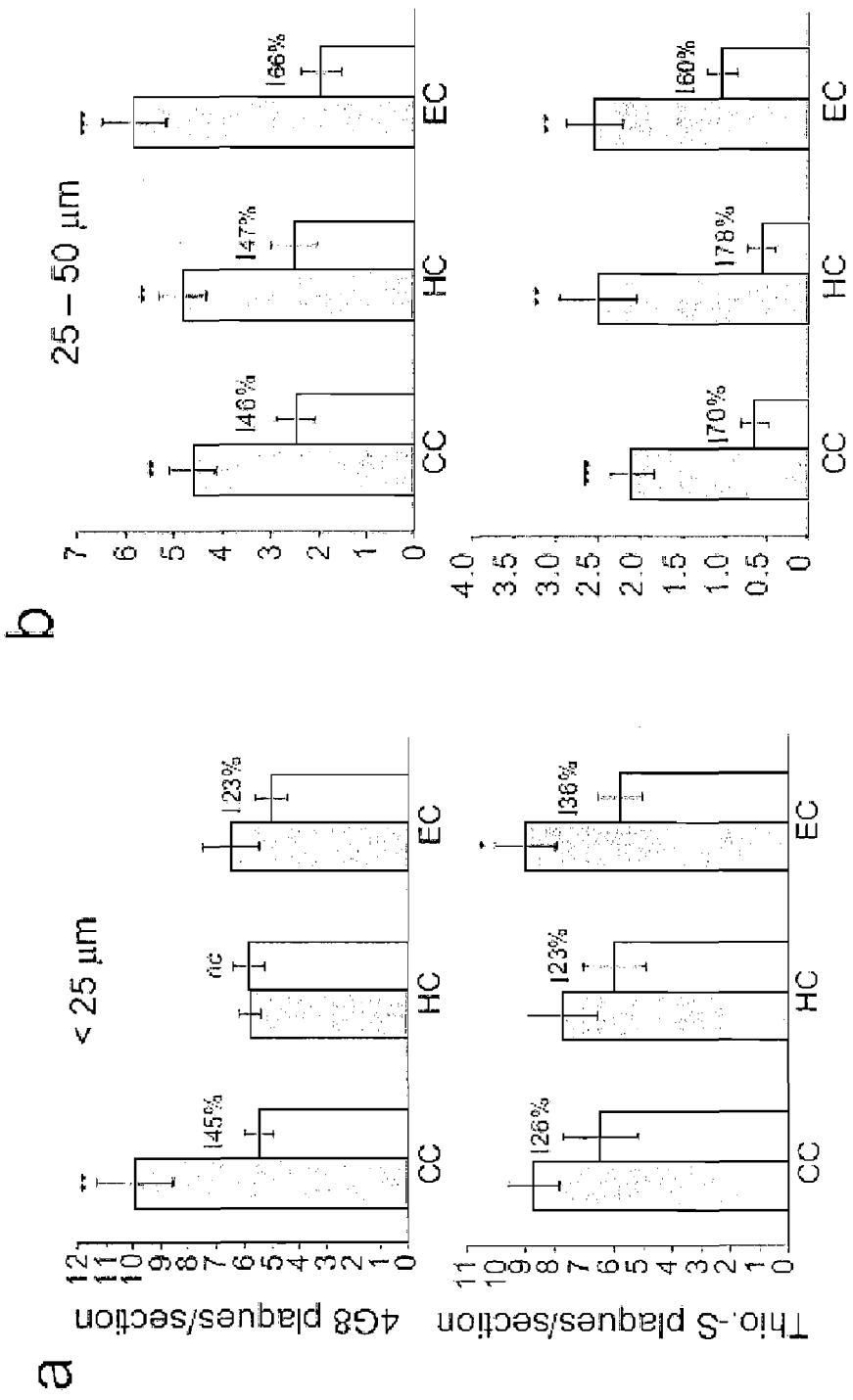
FIG. 4, comprising
Figure 4:
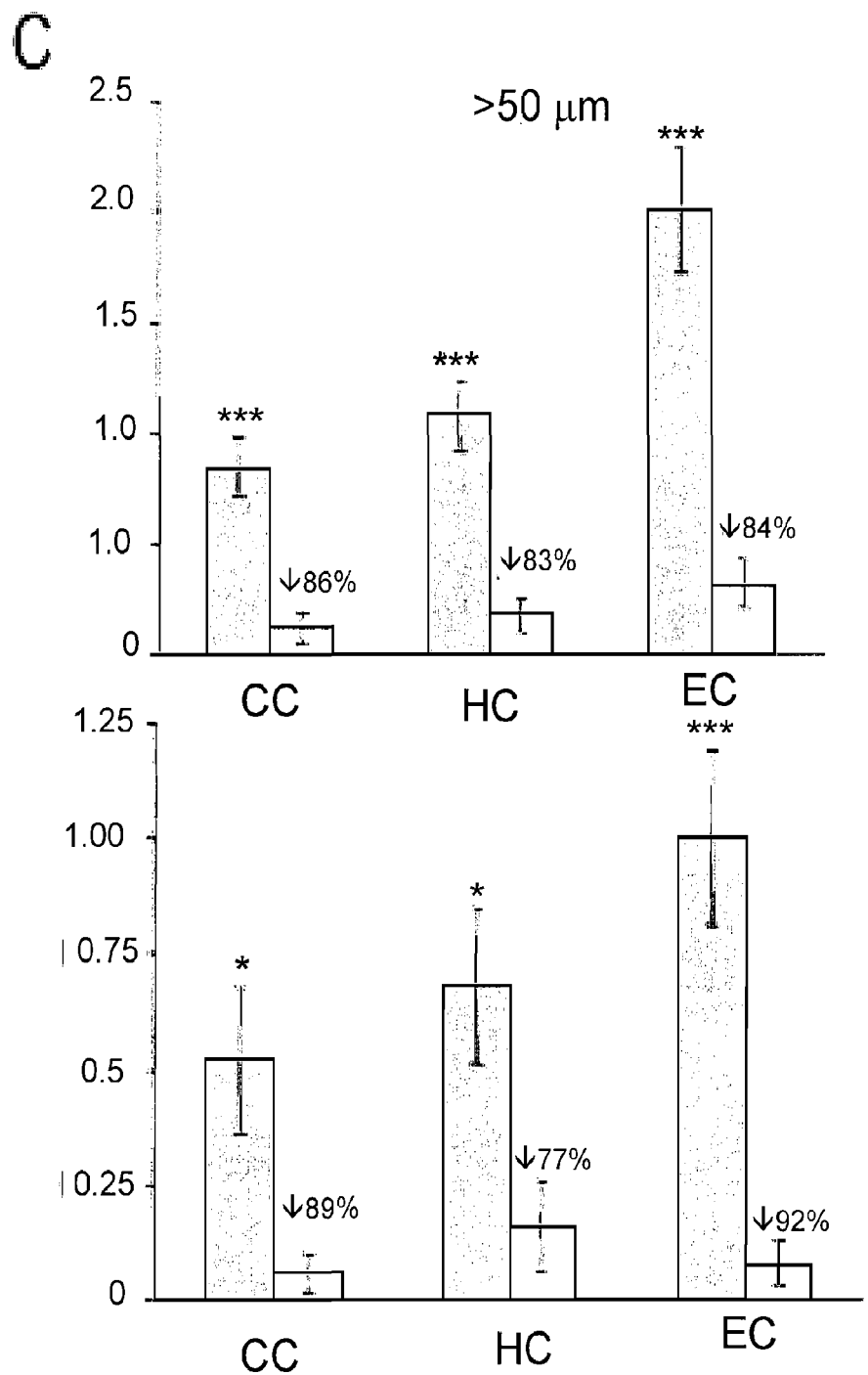
Figure 4:
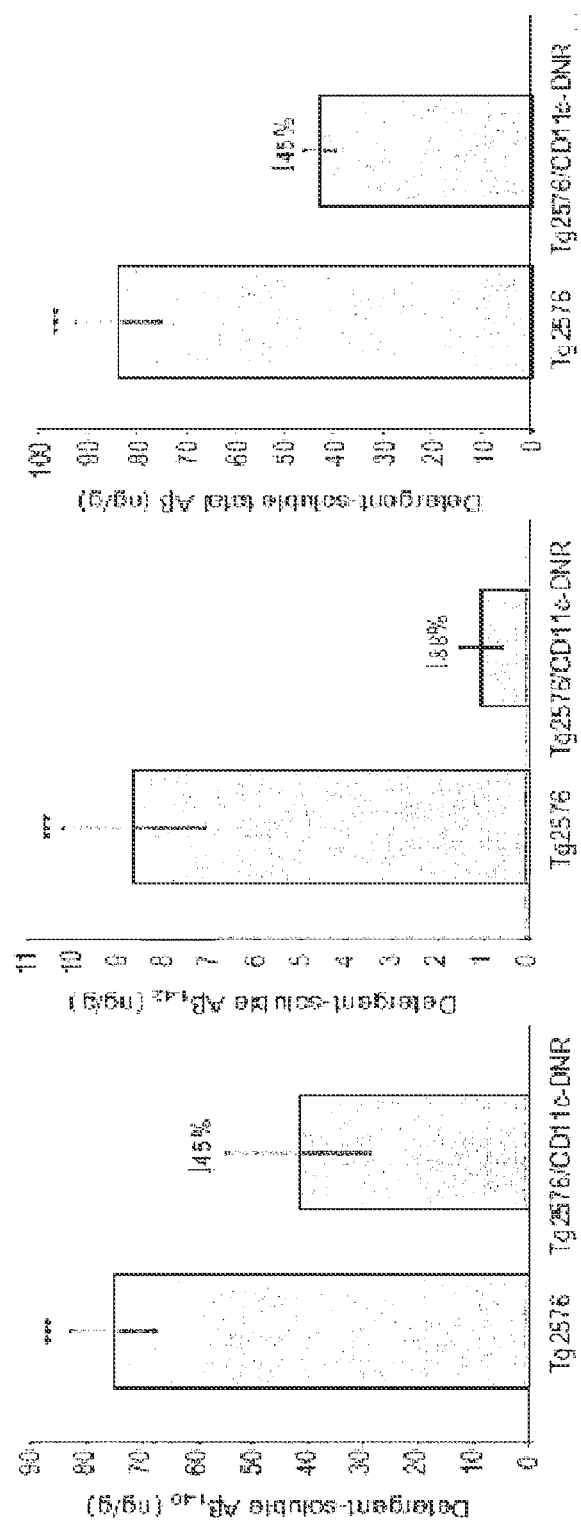
Figure 4:
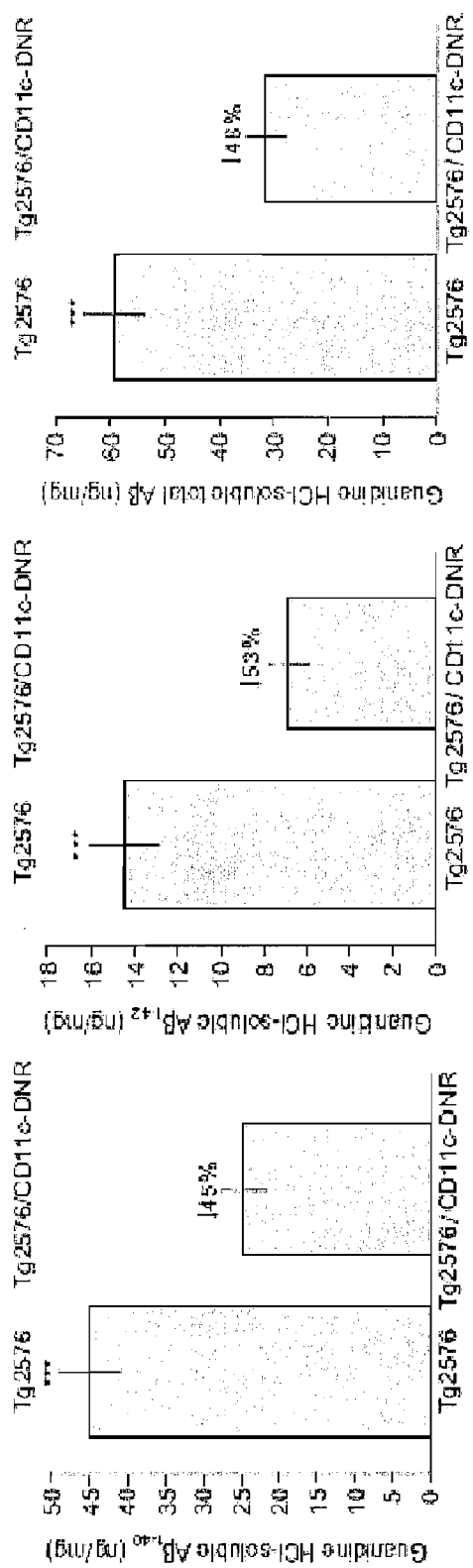
Figure 4:
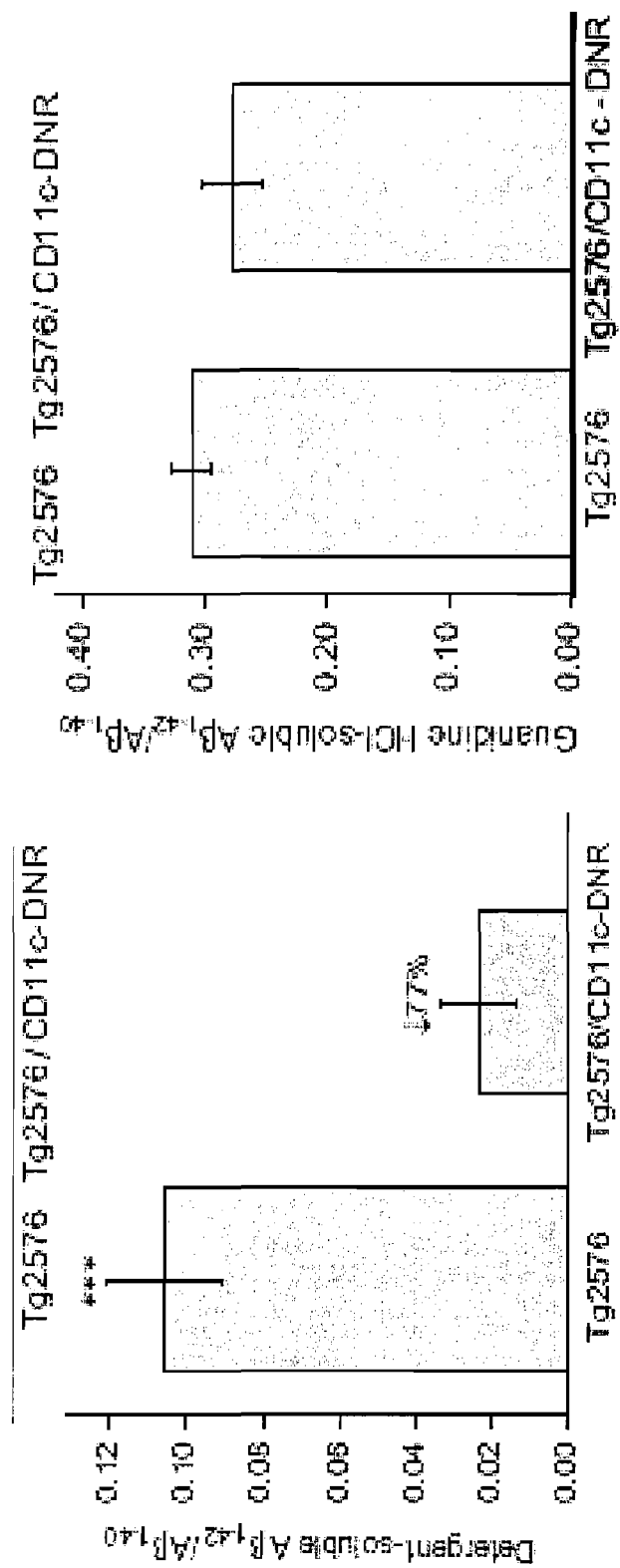
Figure 4:
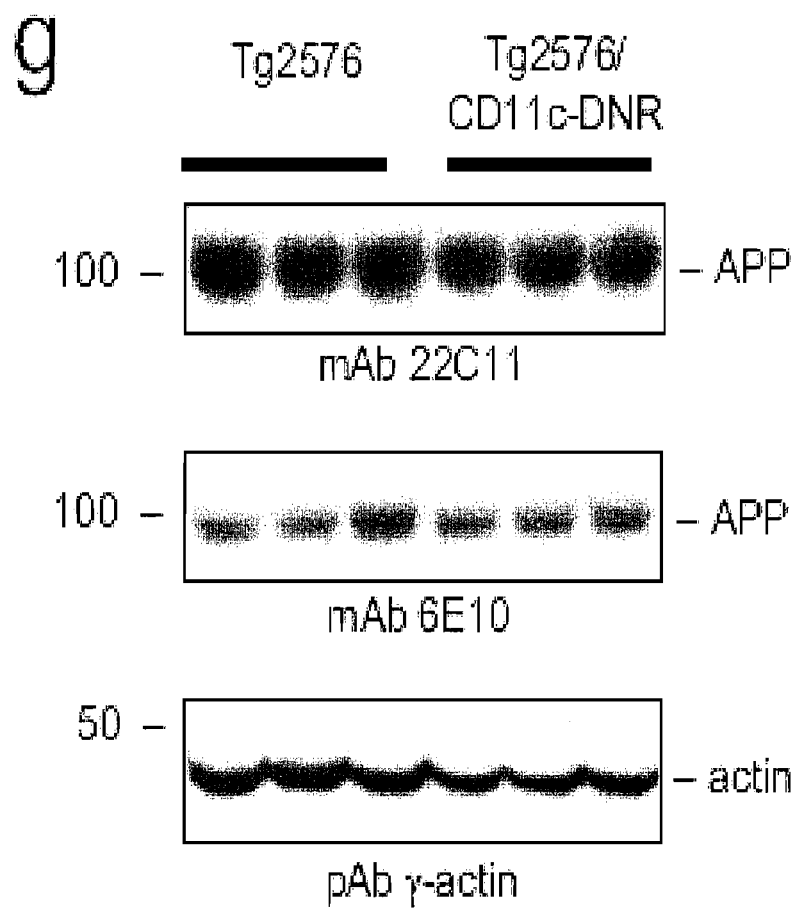
Figure 4:
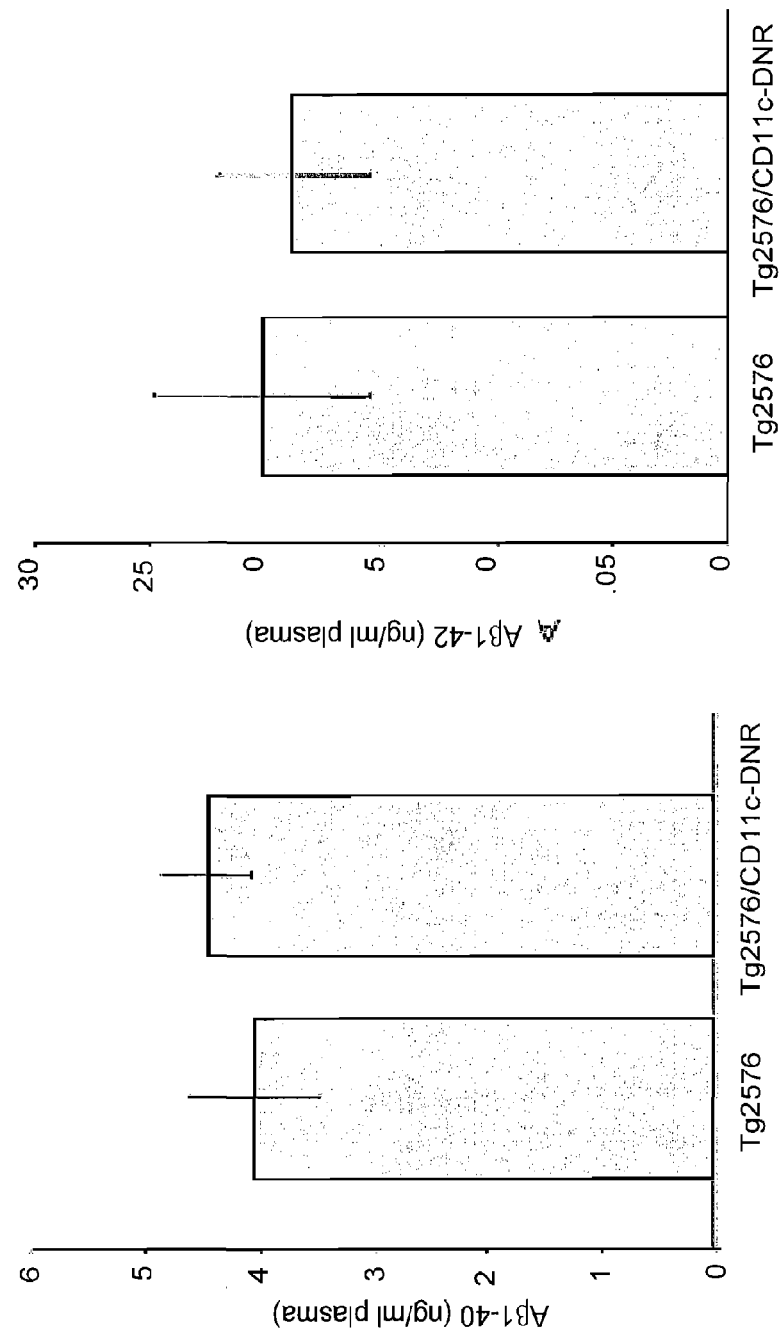
Figure 4:
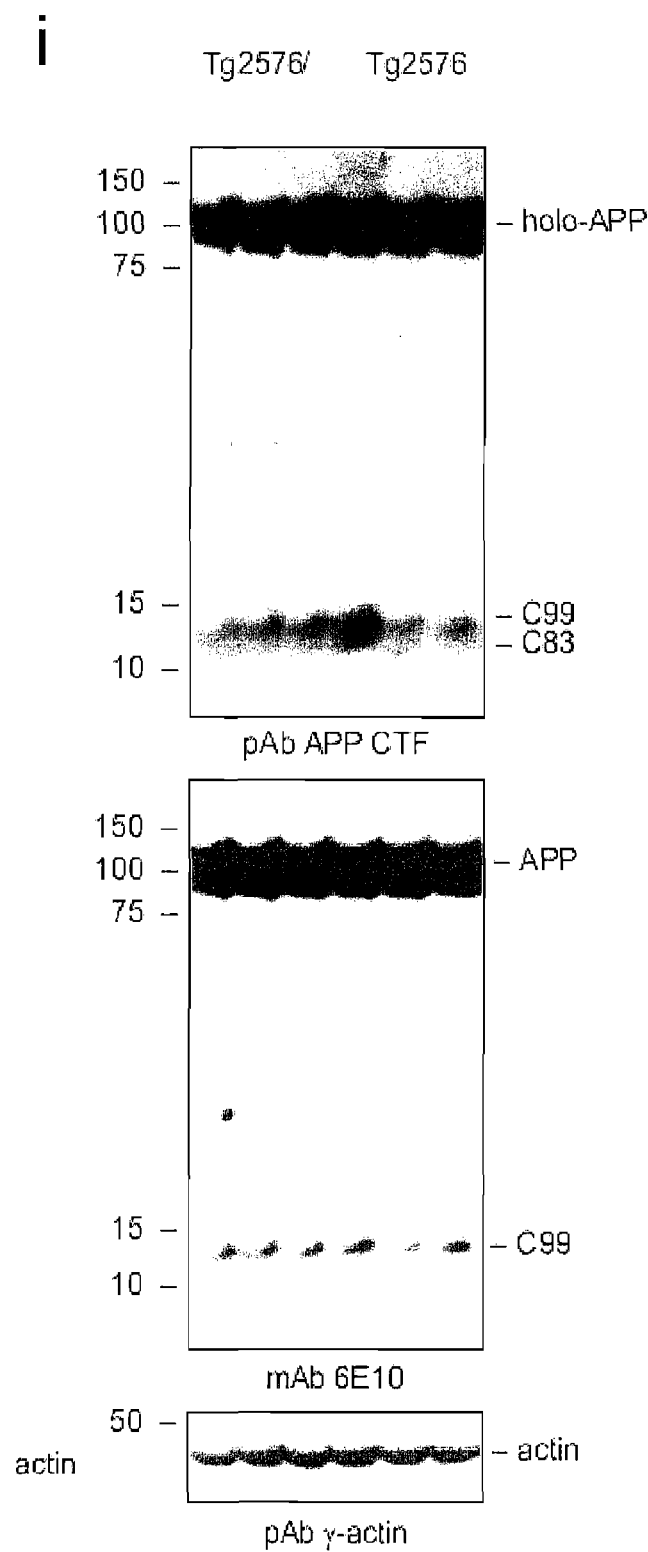

Eighty-three percent of subjects with Alzheimer's disease present with cerebrovascular β-amyloid deposits (cerebral amyloid angiopathy (CAA)) (Ellis et al., 1996, Neurology, 46 (6):1592-6). Tg2576 mice also develop age-dependent vascular β-amyloid deposits (Robbins et al., 2006, J. Neurosci 26:365-371), which were reduced by 62-90% in Tg2576-CD11c-DNR mice compared to Tg2576 mice (FIG. 3C). Biochemical analysis revealed Tg2576-CD11c-DNR mouse reductions in both Aβ1-40 and Aβ1-42 abundance versus Tg2576 mice ranging from 45% to 88% reduction in the detergent-soluble fraction and 45% to 53% reduction in the detergent-insoluble (but guanidine-HCl-extractable) fraction (FIG. 4D, 4E, $P<0.001$). Notably, although the detergent-soluble Aβ1-42/Aβ1-40 ratio was significantly ($P<0.001$) reduced by 77% in Tg2576-CD11c-DNR mice, the Aβ1-42/Aβ1-40 ratio of guanidine-1-HCl-soluble material was not (FIG. 4F).

A reduction in Tg2576-CD11c-DNR mouse cerebral amyloidosis could be due to attenuated APP expression, increased brain-to-blood clearance of Aβ (DeMattos et al., 2002, Science 295:2264-2267), reduced amyloidogenic APP metabolism or activation of endogenous brain Aβ clearance. Brain homogenates from Tg2576 and Tg2576-CD11c-DNR mice were probed for APP but differences in APP abundance between the two strains were not detected (FIG. 4G). Blood-circulating Aβ1-40 and Aβ1-42 species abundance was also assayed and no differences were observed (FIG. 4H). To address steady-state APP metabolism, amyloidogenic carboxyl (C)-terminal APP fragment (β-CTF, C99) and non-amyloidogenic CTF (α-CTF, C83) abundance were analyzed, but again no observable differences between the two strains were detected (FIG. 4I), thus turning the attention to endogenous brain Aβ clearance.

Figure 5:
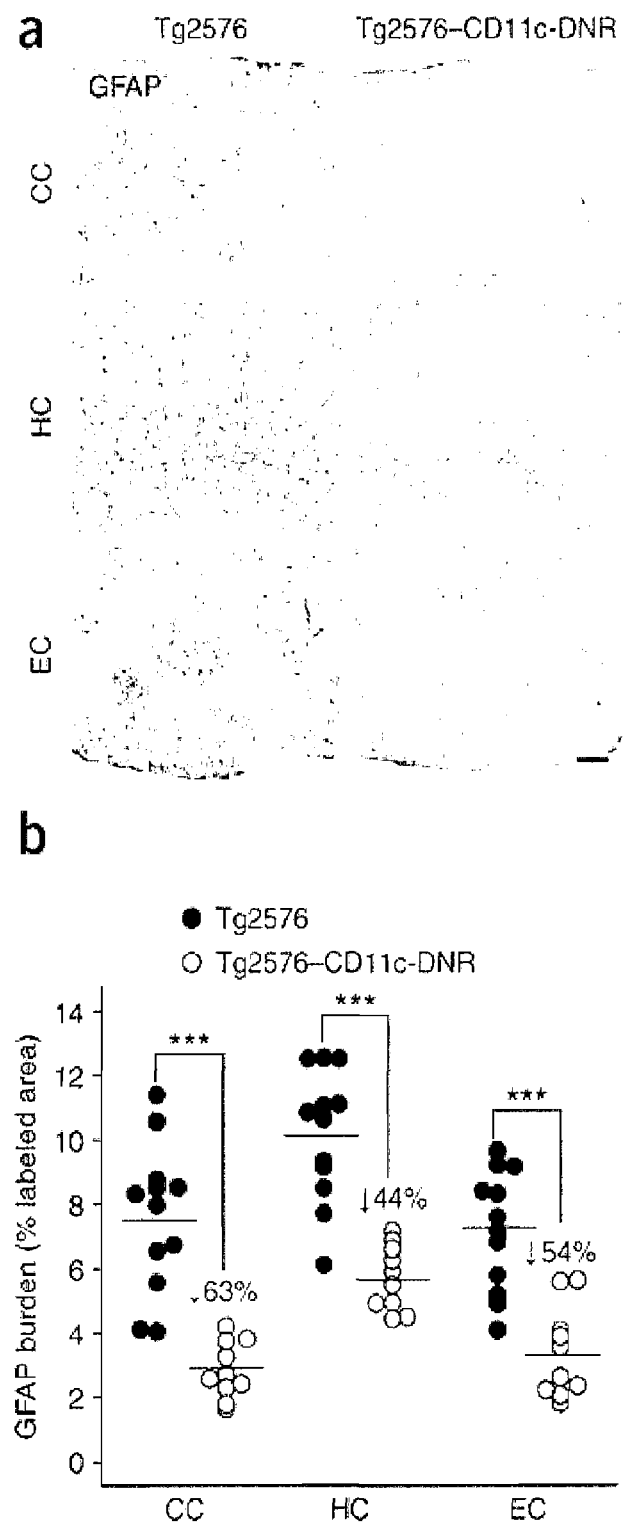
FIG. 5, comprising FIGS. 5A-5E, demonstrates that the CD11c-DNR transgene reduces astrocytosis but increases infiltrating macrophages in Alzheimer's disease mouse models.
Figure 5:
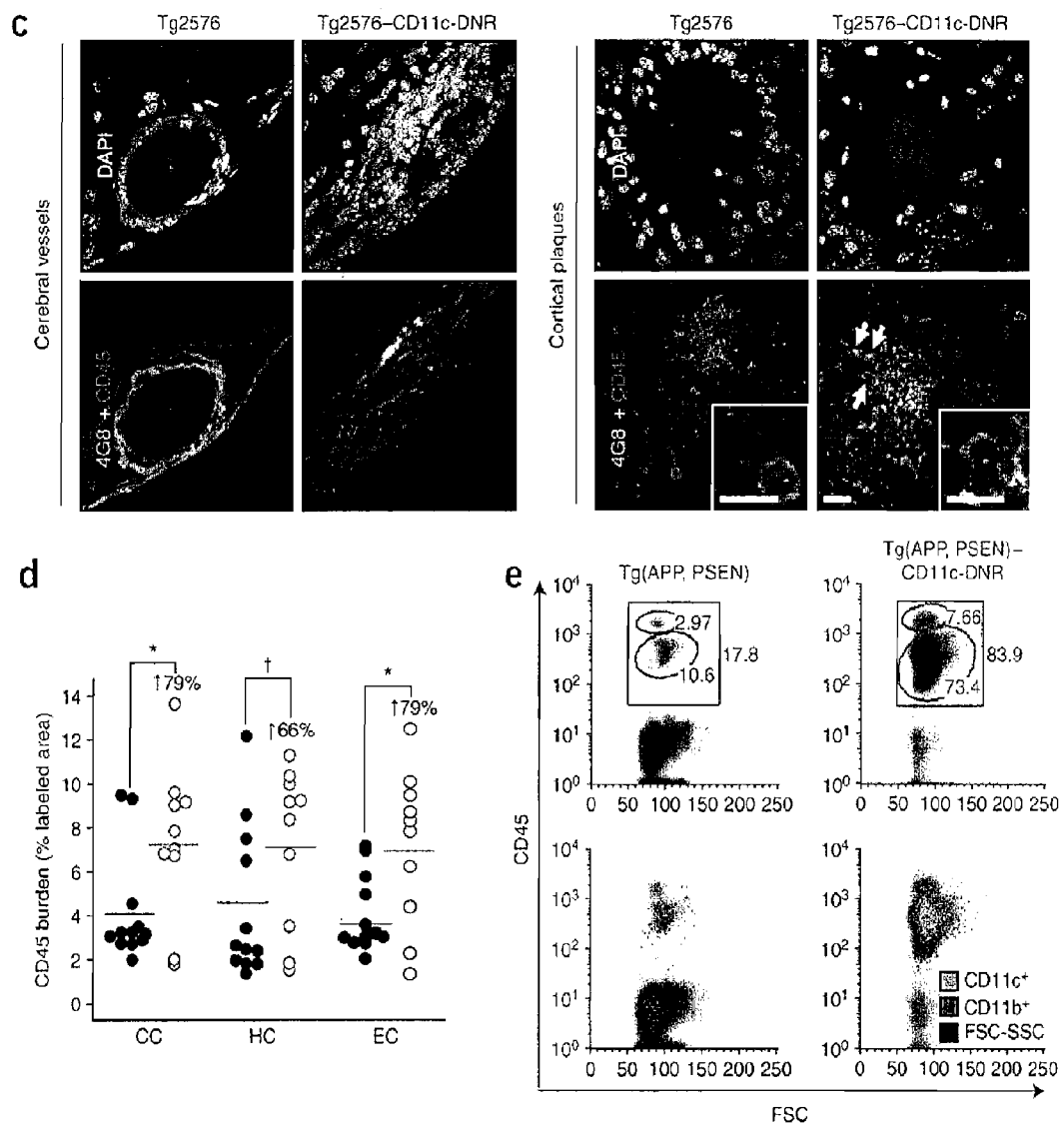
Figure 6:
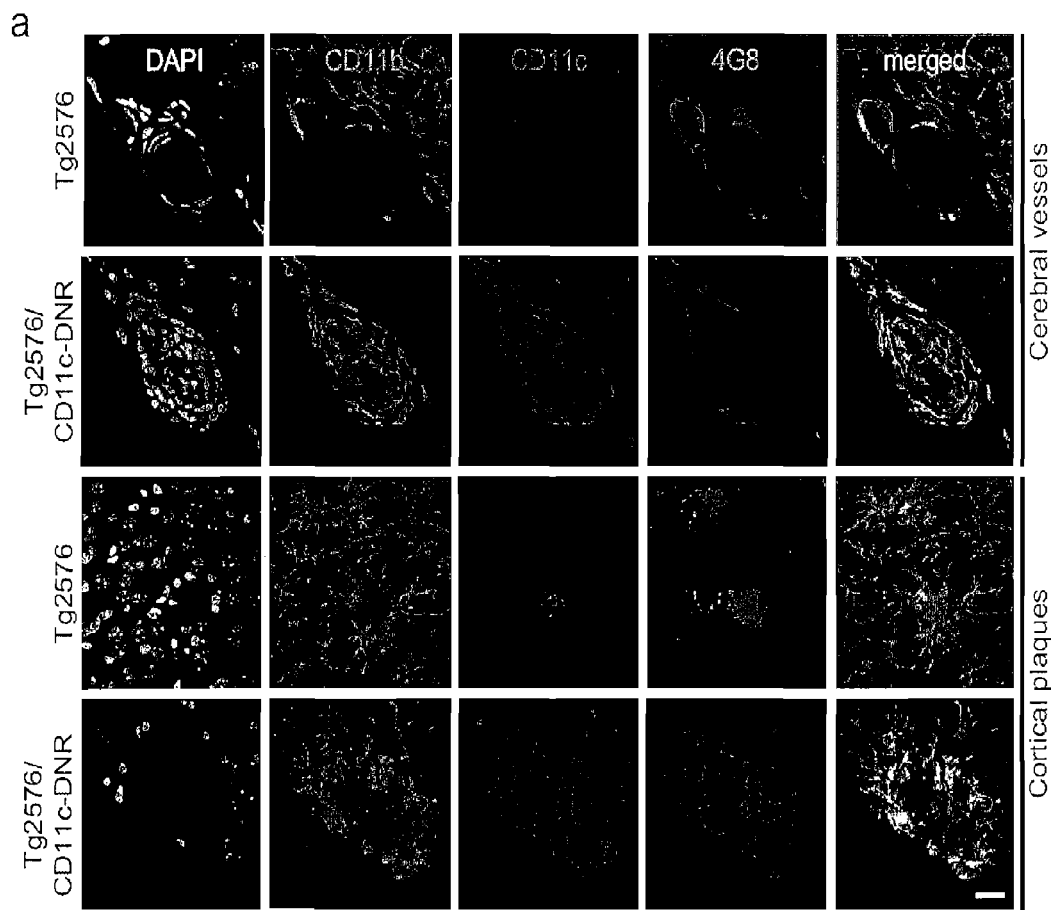
FIG. 6, comprising
Figure 6:
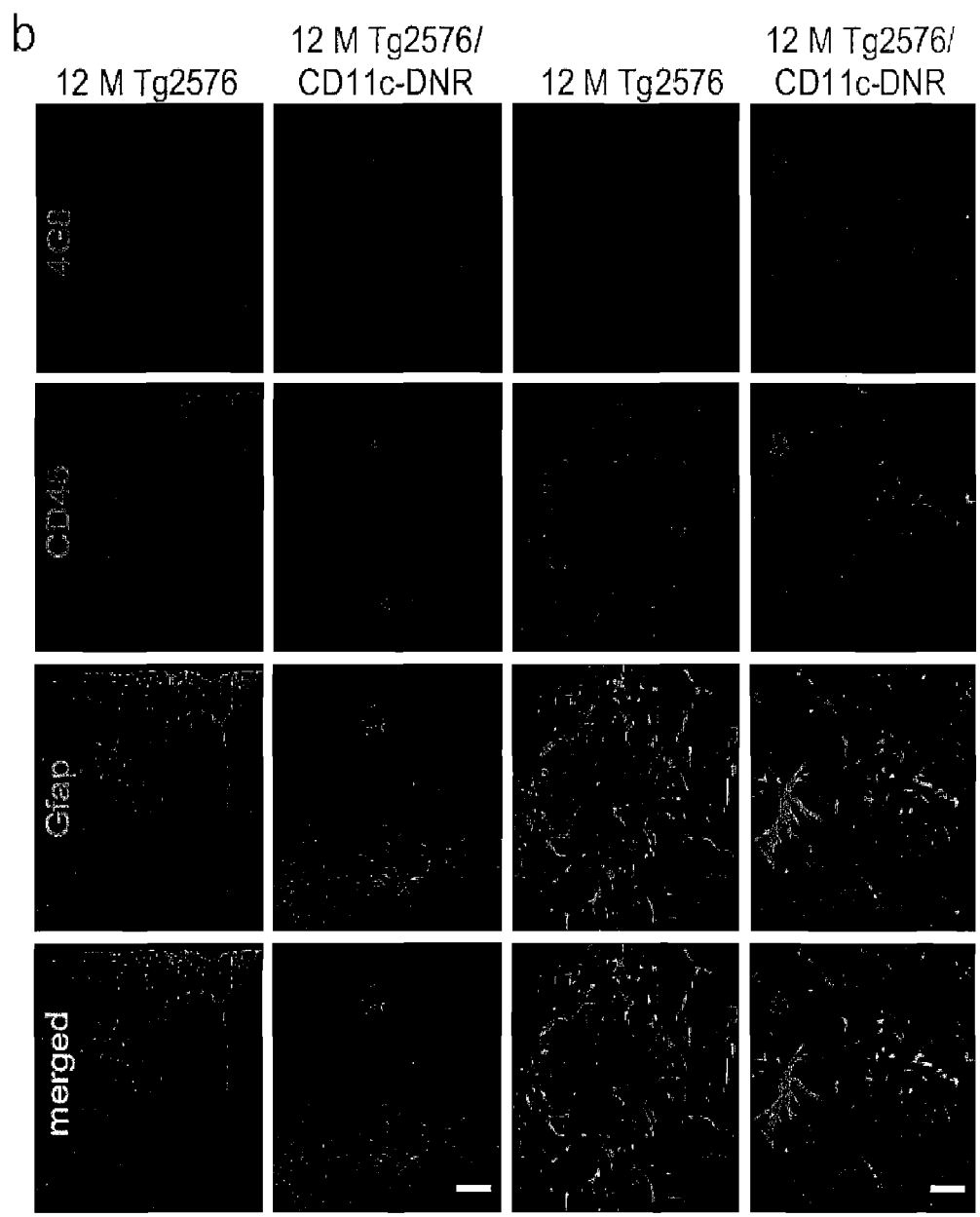

Without wishing to be bound by any particular theory, it is believed that, if the CD11c-DNR transgene affects endogenous brain Aβ clearance, this would probably occur through modulation of brain inflammatory and immune responses. Substantial reductions in the number of activated glial fibrillary acidic protein (GFAP)-positive astrocytes by 44-63% in Tg2576-CD11c-DNR mice versus Tg2576 mice (FIG. 5A, 5B) was noted. Confocal microscopy for CD45, a leukocyte marker also expressed by activated microglia (Lemere et al., 2000, Ann. NY Acad. Sci 920:328-331), revealed numerous round cells in and around cerebral vessels in Tg2576-CD11c-DNR mice that were nearly absent in Tg2576 littermates (FIG. 5C). These cells had few or no processes and were also found in close vicinity to β-amyloid plaques, where they often co-localized with Aβ deposits and sometimes contained Aβ (FIG. 5C). These cells were CD11b+CD11c+ (FIG. 6A), stained positively for the macrophage and activated microglia marker CD68 (data not shown) and were increased in number by 66-79% in Tg2576-CD11c-DNR mice (FIG. 5D). A younger (12-month-old) cohort of mice showed 2-4 β-amyloid plaques per brain section and modest microglial and astrocytic activation that was comparable between Tg2576 and Tg2576-CD11c-DNR mice (FIG. 6B). Of note, round CD45+ cells were not detected in either Tg2576 or Tg2576-CD11c-DNR mice at this age (FIG. 6B), suggesting that this relatively low level of cerebral amyloidosis does not meet a threshold limit for recruiting these cells.

To better characterize these cells, an accelerated Alzheimer's disease mouse model bearing both mutant APP and presenilin-1 transgenes [designated Tg(APP,PSEN); Jankowsky et al., 2001, Biomol. Eng 17:157-165] was crossed with CD11c-DNR mice and FACS analysis of brains from aged progeny was performed. CD45+CD11b+CD11c+ cell numbers were greatly increased in Tg(APP,PSEN)-CD11c-DNR mouse brains (FIG. 5E and FIG. 11, $P<0.01$). Similar to the cells from Tg2576-CD11c-DNR mice, these cells most closely resembled brain-infiltrating macrophages that became 'sensitized' by the CD11c-DNR transgene to enter Alzheimer's disease-like brains.

Two functionally distinct subpopulations of monocytes exist: the proinflammatory (Ly-6C+) and anti-inflammatory (Ly-6C−) subsets (Geissmann et al., 2003, Immunity 19:71-82). It was noted that a majority (>90-95%) of CD45+ cells in Tg(APP,PSEN)-CD11c-DNR mice were Ly-6C− (FIG. 8A). Brain infiltration by these cells seems to occur in response to increasing cerebral amyloidosis, as they are not detected in brains of CD11c-DNR mice (data not shown) or Tg2576-CD11c-DNR mice at a younger age (12 months, FIG. 6B) and do not accumulate in the periphery of Tg(APP,PSEN)-CD11c-DNR mice (FIG. 8B).

Figure 7:
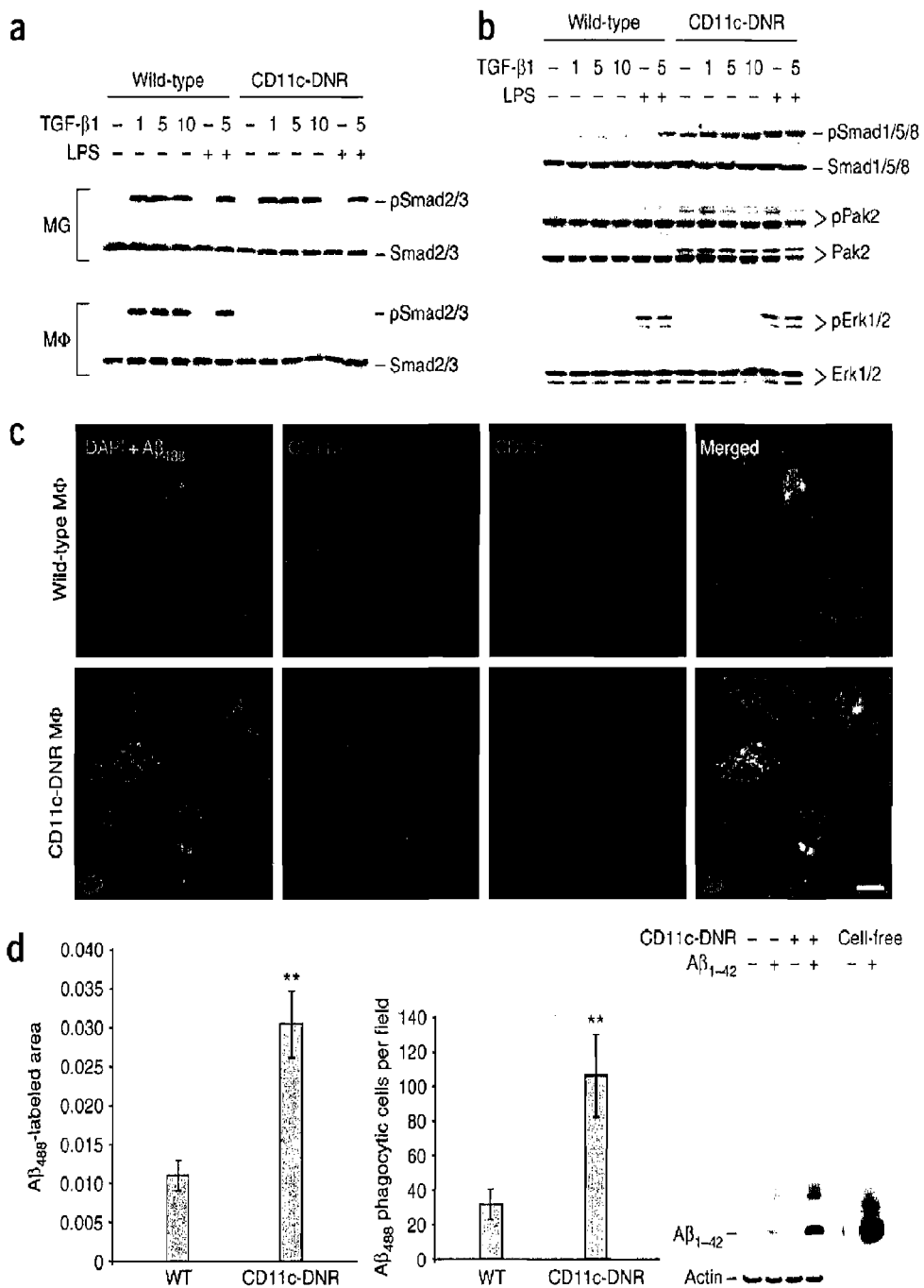
FIG. 7, comprising

CD11c expression by microglia in Tg2576 mice was not detected (FIG. 6A). Additionally, CD11c-DNR transgene mRNA levels trended toward an increase in Tg2576-CD11c-DNR versus CD11c-DNR mouse brains [quantitative real-time PCR unitless ratio of CD11c-DNR/hypoxarithine phosphoribosyltransferase 1 (Hprt1)±s.e.m.: 11.8±3.7 versus 6.6±0.9; P=0.10], and CD11c-DNR mRNA was detected in peripheral macrophages but not in microglia (data not shown). To determine whether TGF-β signaling was reduced in peripheral macrophages or microglia, primary peripheral macrophage cultures from wild-type and CD11c-DNR mice were challenged with a dose range of TGF-β1 and with immunostimulatory lipopolysaccharide (LPS). Wild-type microglia and macrophages showed phosphorylated Smad2/3 (Li et al., 2005 Annu. Rev. Immunol, 24: 99-146) after TGF-β1 challenge, and whereas CD11c-DNR microglia also responded to challenge, CD11c-DNR macrophages were nonresponsive (FIG. 7A). In the relative absence of TGF-β-activated Smad2/3 signaling, constitutively increased phosphorylation of the parallel bone morphogenic protein-activated Smad1/5/8-p21-activated protein kinase pathway (Li et al., 2006, Annu Rev Immunol. 24:99-146) was evident in CD11c-DNR macrophages (FIG. 7B). Exogenous TGF-β1 and LPS further augmented Smad1/5/8 phosphorylation; however, CD11c-DNR macrophages did not show increased extracellular signal-related kinase-1/2 phosphorylation in response to general LPS activation (FIG. 7B).

Peripheral macrophages from wild-type and CD11c-DNR mice were pulse-chased with fluorescently tagged Aβ1-42 (Aβ488) to test for Aβ phagocytosis. Notably, quantitative confocal microscopy analyses revealed approximately three-fold increased Aβ488 phagocytosis in CD11c-DNR macrophages as compared to wild-type macrophages, which was not altered by the presence of the fluorescent Aβ1-42 tag (FIG. 7C, 7D). Both monomeric and oligomeric species of Aβ1-42 could be detected in greater quantities in CD11c-DNR macrophages than in wild-type cells (FIG. 7D), suggesting that CD11c-DNR macrophages engulfed AD species irrespective of aggregation status.

To further validate results from a genetic approach, two activin-like kinase 5 (ALK5, a key TGF-β receptor I that pairs with TGF-β receptor II for signaling) inhibitors were used: SB-505124 and SB-431542 (Tesseur et al., 2006, J Clin Invest. 116 (11):3060-9). Treatment of peripherally isolated macrophages with exogenous TGF-β1 increased phosphorylation of both Smad2/3 and Smad1/5/8, and this effect on Smad2/3 phosphorylation was blocked by ALK5 inhibition in a dose-dependent manner (FIG. 9A). Of note, ALK5 inhibitor treatment alone increased the ratio of phospho-Smad1/5/8 to phospho-Smad2/3, which was associated with increased Aβ phagocytosis in a dose-dependent fashion (FIG. 9A-9C). Thus, both genetic and pharmacologic means of TGF-β signaling inhibition promoted increased macrophage Aβ phagocytosis.

Exogenous addition of TGF-β1 to microglia promotes increased Aβ uptake (Wyss-Coray, et al., 2001, Nat Med. 7 (5):612-18), raising an apparent discrepancy with the findings presented herein. The results presented herein were reproducible in both wild-type microglia (data not shown) and wild-type macrophages. Notably, it was observed that either the CD11c-DNR transgene or ALK5 inhibitors promoted blockade of TGF-β-activated Smad2/3 phosphorylation, but they promoted increased phosphorylation of alternate Smad1/5/8 signaling pathway molecules in macrophages, which is further inducible by exogenous TGF-β1 (FIG. 7A, 7B and FIG. 9A). Thus, activation of the alternate Smad1/5/8 signaling cascade in response to TGF-β may resolve this apparent discrepancy. Without wishing to be bound by any particular theory, it seems that the act of blocking Smad2/3 signaling results in promotion of Smad 1/5/8 signaling, which is associated with increased macrophage Aβ phagocytosis.

To determine if the act of directly activating alternate Smad1/5/8 signaling by means of contacting peripheral macrophages with bone morphogenic proteins, peripheral macrophages were first elicited with thioglycollate and then isolated from peritoneal cavities of wild-type mice as described elsewhere herein. As shown in FIG. 12A, these isolated cells expressed the macrophage markers F4/80 antigen, CD11b, and CD11c by flow cytometry. Peripheral macrophages went unstimulated (control), or were stimulated with TGF-β1 (5 ng/mL) in the presence or absence of a dose range of recombinant bone morphogenic protein (BMP)-2 (50, 100, or 200 ng/mL) or recombinant BMP-4 (12.5, 25, or 50 ng/mL) to allow for assessment of phosphorylation (activation) of canonical TGF-β-activated Smad2/3 or bone morphogenic protein-activated Smad1/5/8 and PAK2. As depicted in FIG. 12B, TGF-β1 treatment alone promoted Smad2/3 phosphorylation but had little impact on Smad1/5/8 phosphorylation or PAK2 phosphorylation. On the other hand, BMP-2 and BMP-4 promoted Smad1/5/8 phosphorylation and PAK2 phosphorylation but did not impact Smad2/3 phosphorylation. Interestingly, the addition of TGF-β1 to the BMP treatment conditions further promoted Smad2/3 phosphorylation but inhibited BMP-induced PAK2 phosphorylation. As depicted in FIG. 2B (lower panel), monotreatment with either BMP-2 or BMP-4 increased the ratio of pSmad1/5/8 to pSmad2/3 compared with TGF-β1 treatment alone. As depicted in FIG. 12C, this increased ratio of pSmad1/5/8 to pSmad2/3 after BMP monotreatment (particularly at 50 ng/mL for BMP-2 and 12.5 ng/mL for BMP-4) is associated with increased phagocytosis of Aβ488 according to methods described elsewhere herein and assayed by flow cytometry.

Although Tg2576-CD11c-DNR mice had substantial reductions in detergent-soluble and guanidine HCl-soluble Aβ1-42 and detergent-soluble Aβ1-42/Aβ1-40 ratio, guanidine HCl-soluble Aβ1-42/Aβ1-40 ratio was apparently unaltered. When comparing male and female Tg2576 mice, it was observed that females had greater behavioral impairment than males (FIG. 2A-2C). Female Tg2576 mice had increased detergent-soluble and guanidine HCl-soluble Aβ1-42 and increases in both detergent-soluble and guanidine HCl-soluble Aβ1-42/Aβ1-40 ratio (FIG. 9D, 9E). Insoluble Aβ is probably primarily responsible for Tg2576-associated Morris water maze impairment (Westerman et al., 2002, J. Neurosci 22:1858-1867), and the data presented herein suggest that the ratio of more aggregated Aβ1-42/Aβ1-40 is particularly crucial for this behavioral phenotype.

The results presented herein imply that reduction of TGF-β signaling in peripheral macrophages promotes increased brain infiltration of blood-derived macrophages and Aβ clearance in Alzheimer's disease mice. The next set of experiments was designed to determine whether infiltration is associated with a proinflammatory response, as was observed after active Aβ vaccination in subjects with Alzheimer's disease (Nicoll et al., 2003, Nat. Med 9:448-452). It was observed that a panel of proinflammatory cytokines in brain homogenates from Tg2576 and Tg2576-CD11c-DNR mice were either unchanged between groups or significantly lower in Tg2576-CD11c-DNR mice (data not shown). Furthermore, it was observed that there were reduced levels of proinflammatory tumor necrosis factor-α mRNA in Tg2576 and Tg2576-CD11c-DNR mice compared to wild-type mice, and increased levels of anti-inflammatory interleukin-10 mRNA in Tg2576-CD11c-DNR brains compared to wild-type mice (FIG. 9F), suggesting that infiltrating CD11c-DNR macrophages are shifted to an anti-inflammatory phenotype endorsing Aβ Phagocytosis (Town et al., 2005, J. Neuroinflammation 2:24).

The next set of experiments were designed to determine whether infiltration requires blockade of TGF-β signaling and whether the blockage is sufficient for peripheral macrophages to routinely enter Alzheimer's disease mouse brains and limit cerebral amyloidosis. Reports suggest that brain infiltration of blood-derived macrophages occurs to a limited extent. For example, blood-derived monocytes have been found near cerebral vessels and β-amyloid plaques (Stalder et al., 2005, J. Neurosci 25:11125-11132), and ablation of these cells increases cerebral amyloidosis (Simard et al., 2006, Neuron 49:489-502; El Khoury et al., 2007, Nat. Med 13:432-438). These effects seem specific to Alzheimer's disease mice, as recent approaches did not show similar results after CNS injury unless the mice were irradiated (Ajami et al., 2007, Nat. Neurosci 10:1538-1543; Mildner et al., 2007, Nat. Neurosci 10:1544-1553). It is believed that future studies designed to establish chimeric mice without using irradiation will be useful to directly evaluate brain entry of peripheral monocytes and macrophages. Nonetheless, the results presented herein dovetail with findings that peripheral, blood-derived macrophages can clear cerebral Aβ, as blocking TGF-β signaling on peripheral macrophages leads to en masse brain infiltration and beneficial cerebral Aβ clearance. Notably, TGF-β signaling inhibitors may either be beneficial or deleterious depending on where the inhibition is targeted (that is, directly in the CNS (Tesseur et al., 2006, J Clin Invest. 116 (11):3060-9) or in the periphery). Yet, the results presented herein demonstrate that inhibition of TGF-β signaling on peripheral monocytes and macrophages represent an advantageous anti-amyloid therapeutic approach for Alzheimer's disease.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of enhancing macrophage Aβ phagocytosis activity of a peripheral macrophage of a mammal with Alzheimer's disease, the method comprising contacting the peripheral macrophage of the mammal with Alzheimer's disease with an inhibitor of a component of TGF-β signaling pathway and with an activator of a component of bone morphogenic protein-Smad1/5/8-PAK2 signaling pathway, wherein the inhibitor of a component of TGF-β signaling pathway is at least one selected from the group consisting of dominant negative TGF-β receptor, a nucleic acid encoding a dominant negative TGF-β receptor, SB-505124 and SB-431542, and wherein the activator of a component of bone morphogenic protein-Smad1/5/8-PAK2 signaling pathway is at least one selected from the group consisting of BMP-2, BMP-4, a nucleic acid encoding BMP-2, and a nucleic acid encoding BMP-4, thereby inducing the peripheral macrophage to infiltrate the central nervous system (CNS) of the mammal.

2. The method of claim 1, wherein said TGF-β signaling pathway is TGF-β-Smad2/3 signaling pathway.

3. The method of claim 1, wherein said inhibitor of a component of TGF-β signaling pathway inhibits activin-like kinase 5 (ALK5).

* * * * *